United States Patent
Kato et al.

(10) Patent No.: US 11,306,152 B2
(45) Date of Patent: Apr. 19, 2022

(54) ANTI-PODOPLANIN ANTIBODY

(71) Applicants: Tohoku University, Miyagi (JP); Zenogen Pharma Co., Ltd., Fukushima (JP)

(72) Inventors: Yukinari Kato, Miyagi (JP); Mika Kato, Miyagi (JP); Shinji Yamada, Miyagi (JP); Satoshi Ogasawara, Miyagi (JP); Takuro Nakamura, Miyagi (JP)

(73) Assignees: Tohoku University, Miyagi (JP); Zenogen Pharma Co., Ltd., Fukushima (JP)

( * ) Notice: Subject to any disclaimer, the term of this patent is extended or adjusted under 35 U.S.C. 154(b) by 123 days.

(21) Appl. No.: 16/498,411

(22) PCT Filed: Mar. 30, 2017

(86) PCT No.: PCT/JP2017/013488
§ 371 (c)(1),
(2) Date: Sep. 27, 2019

(87) PCT Pub. No.: WO2018/179302
PCT Pub. Date: Oct. 4, 2018

(65) Prior Publication Data
US 2021/0115151 A1 Apr. 22, 2021

(51) Int. Cl.
*C07K 16/30* (2006.01)
*A61K 39/00* (2006.01)

(52) U.S. Cl.
CPC ........ *C07K 16/30* (2013.01); *A61K 2039/505* (2013.01); *C07K 2317/565* (2013.01)

(58) Field of Classification Search
CPC .... C07K 16/30; C07K 16/3092; C07K 16/28; C07K 16/36; C07K 2317/76; C07K 2317/565; C07K 16/464; A61P 35/00
See application file for complete search history.

(56) References Cited

U.S. PATENT DOCUMENTS

| 2016/0347834 A1 | 12/2016 | Kato |
| 2018/0237518 A1 | 8/2018 | Fujita |

FOREIGN PATENT DOCUMENTS

| EP | 2484697 A1 | 8/2012 |
| WO | 2015053381 A1 | 4/2015 |
| WO | 2017010463 A1 | 1/2017 |
| WO | 2017026502 | 2/2017 |

OTHER PUBLICATIONS

Malia et al., Proteins 2016; 84;427-434 (Year: 2016).*
De Genst et al., Developmental and Comparative Immunology, 2006, 30:187-198 (Year: 2006).*
Ward et al. Nature, 1989, 341:544-546 (Year: 1989).*
Barthelemy et al. Journal of Biological Chemistry, 2008, 283:3639-3654 (Year: 2008).*
Choi & Deane, Molecular BioSystems, 2011,7:3327-3334 (Year: 2011).*
Griffiths et al. EMBO Journal, 1993, 12:725-734 (Year: 1993).*
Klimka et al., British Journal of Cancer, 2000, 83:252-260 (Year: 2000).*
Beiboer et al. Journal of Molecular Biology, 2000, 296:833-849 (Year: 2000).*
International Search Report received in PCT/JP2017/013488 dated Jun. 20, 2017.
Written Opinion received in PCT/JP2017/013488 dated Jun. 20, 2017.
Kaneko et al., "Functional glycosylation of human podoplanin: glycan structure of platelet aggregation-inducing factor", Jan. 23, 2007, pp. 331-336, vol. 581, No. 2, Publisher: FEBS Lett.
Sekiguchi et al., "Targeting a novel domain in podoplanin for inhibiting platelet-mediated tumor metastasis", Jan. 26, 2016, p. 39343946, vol. 7, No. 4, Publisher: Oncotarget.
Kaneko et al., "Antitumor activity of chLpMab2, a human-mouse chimeric cancer-specific antihuman podoplanin antibody, via antibody-dependent cellular cytotoxicity", Mar. 23, 2017, p. 768777, vol. 6, No. 4, Publisher: Cancer Med.
Kato et al., "A cancer-specific monoclonal antibody recognizes the aberrantly glycosylated podoplanin", Aug. 1, 2014, p. 5924, vol. 2014, No. 4, Publisher: Sci Rep.
Kato et al., "The chimeric antibody chLpMab-7 targeting human podoplanin suppresses pulmonary metastasis via ADCC and CDC rather than via its neutralizing activity", Nov. 3, 2015, p. 3600336018, vol. 6, No. 34, Publisher: Oncotarget.
Kato et al., "LpMab-12 Established by CasMab Technology Specifically Detects Sialylated OGlycan on Thr52 of Platelet Aggregation-Stimulating Domain of Human Podoplanin" Mar. 31, 2016, p. e0152912, vol. 11, No. 3, Publisher: PLoS One.

* cited by examiner

*Primary Examiner* — Karen A. Canella
(74) *Attorney, Agent, or Firm* — Suzannah K. Sundby, Esq.; Canady + Lortz LLP

(57) ABSTRACT

The present invention provides a cancer cell-specific anti-podoplanin antibody or an antigen-binding fragment thereof having an epitope in a Thr85-containing region of an amino acid sequence of human podoplanin represented by SEQ ID NO: 1, the Thr85 having a sialylated O-glycan added thereto.

18 Claims, 10 Drawing Sheets
Specification includes a Sequence Listing.

[Fig.1]
MWKVSALLFVLGSASLWVLAEGASTGQPEDDTETTGLEGGVAMPGAEDDVVT
PGTSEDRYKSGLTTLVATSVNSVTGIRIEDLPTSESTVHAQEQSPSATASNVATS
HSTEKVDGDTQTTVEKDGLSTVTLVGIIVGVLLAIGFIGGIIVVVMRKMSGRYSP
[Fig.2]
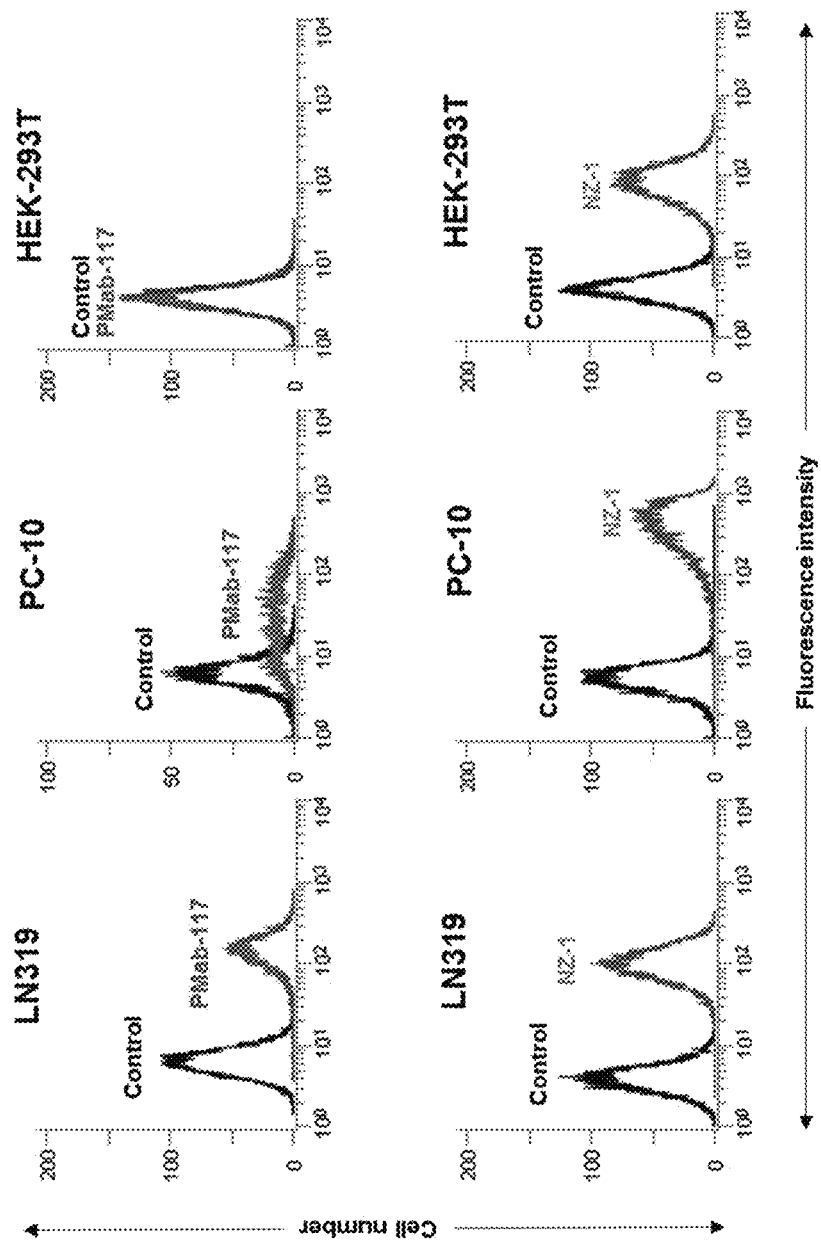

[Fig.3]

ATGTTGGTGCTGCAGTGGGTTTTGGTGACTGCTCTTTTTCAAGGTGTGCATTGTGCGGTG
CAGCTTGTTGAGTCTGGTGGAGGATTGGTGCAGCCTAAGGAGTCATTGAAAATCTCATGT
GCAGCCTCTGGATTCACCTTCAGTAATGCTGCCATGTACTGGGTCCGCCAgGCTCCAGGA
AAGGGTCTGGAGTGGGTTGCTCGCATAAGAAGTAAACCTAATAATTATGCAACATATTATA
CTGATTCAGTGAAAGGCAGATTCACCATCTCCAGAGATGATTCAAAAAGCATGGTCCACC
TACAAATGGATAACTTGAAAACTGAGGACACAGCCATGTATTACTGTACAGTAGGGGCA
ACAACTACGCGGCTGCTTACTGGGGCCAAGGCACTCTGGTCACTGTCTCTTCAGGATCCA
CCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAA
CTCAGGCGCCCTGACCAGCGGCGTGCACACCTTCCCGGCTGTCCTACAGTCCTCAGGAC
TCTACTCCCTCAGCAGCGTGGTGACCGTGCCCTCCAGCAGCTTGGGCACCCAGACCTAC
ATCTGCAACGTGAATCACAAGCCCAGCAACACCAAGGTGGACAAGAAAGTTGAGCCCA
AATCTTGTGACAAAACTCACACATGCCCACCGTGCCCAGCACCTGAACTCCTGGGGGA
CCGTCAGTCTTCCTCTTCCCCCCAAAAACCCAAGGACACCCTCATGATCTCCCGGACCCCT
GAGGTCACATGCGTGGTGGTGGACGTGAGCCACGAAGACCCTGAGGTCAAGTTCAACT
GGTACGTGGACGGCGTGGAGGTGCATAATGCCAAGACAAAGCCGCGGGAGGAGCAGTA
CAACAGCACGTACCGTGTGGTCAGCGTCCTCACCGTCCTGCACCAGGACTGGCTGAATG
GCAAGGAGTACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGCCCCCATCCC
GGGATGAGCTGACCAAGAACCAGGTCAGCCTGACCTGCCTGGTCAAAGGCTTCTATCCC
AGCGACATCGCCGTGGAGTGGGAGAGCAATGGGCAGCCGGAGAACAACTACAAGACCA
CGCCTCCCGTGCTGGACTCCGACGGCTCCTTCTTCCTCTACAGCAAGCTCACCGTGGACA
AGAGCAGGTGGCAGCAGGGGAACGTCTTCTCATGCTCCGTGATGCATGAGGCTCTGCAC
AACCACTACACGCAGAAGAGCCTCTCCCTGTCTCCGGGTAAATGA

[Fig.4]

ATGAAAGTGCCTGTTAGGCTGCTGGTGCTGTTGTTTTGGATTCCAGCTTCCAGAAGTGAT
GTTGTGTTGACACAAACTCCAGTTGCCCAGCCTGTCACACTTGGAGATCAAGCTTCTATA
TCTTGCAGGTCTAGTCAGAGCCTGGTACATAGTAATGGAAACACTTATTTGGAATGGTAC
CTACAGAAGCCAGGCCAGTCTCCACAGCTCCTCATCTATAAGGTTTCCAACCGATTTTCT
GGGGTACCAGACAGGTTCATTGGCAGTGGGTCAGGGTCAGATTTCACCCTCAAGATCAG
CAGAGTAGAGCCTGAGGACTTGGGAGTTTATTACTGTTTCCAAGTTACACATGATCCATT
CACGTTCGGCTCAGGGACGAAGTTGGAAATAAAACGGGGATCCGCTGCACCATCTGTCT
TCATCTTCCCGCCATCTGATGAGCAGTTGAAATCTGGAACTGCCTCTGTTGTGTGCCTGCT
GAATAACTTCTATCCCAGAGAGGCCAAAGTACAGTGGAAGGTGGATAACGCCCTCCAAT
CGGGTAACTCCCAGGAGAGTGTCACAGAGCAGGACAGCAAGGACAGCACCTACAGCCT
CAGCAGCACCCTGACGCTGAGCAAAGCAGACTACGAGAAACACAAAGTCTACGCCTGC
GAAGTCACCCATCAGGGCCTGAGCTCGCCCGTCACAAAGAGCTTCAACAGGGGAGAGT
GTTAG

[Fig.5]

MLVLQWVLVTALFQGVHCAVQLVESGGGLVQPKESLKISCAASGFTFSNAAMYWVRQAPG
KGLEWVARIRSKPNNYATYYTDSVKGRFTISRDDSKSMVHLQMDNLKTEDTAMYYCTVGG
NNYAAAYWGQGTLVTVSSGSTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKVEPKSCDKT
HTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGK

[Fig.6]

MKVPVRLLVLLFWIPASRSDVVLTQTPVAQPVTLGDQASISCRSSQSLVHSNGNTYLEWYLQ
KPGQSPQLLIYKVSNRFSGVPDRFIGSGSGSDFTLKISRVEPEDLGVYYCFQVTHDPFTFGSGT
KLEIKRGSAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC

[Fig.7]

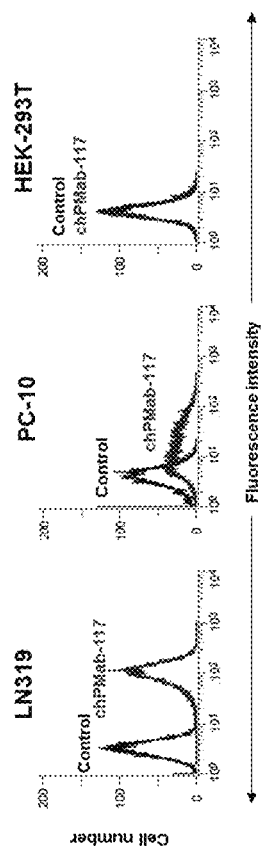

[Fig.8]

ATGTTGGTGCTGCAGTGGGTTTTGGTGACTGCTCTTTTTCAAGGTGTGCATTGTGC
GGTGCAGCTTGTTGAGTCTGGTGGAGGATTGGTGCAGCCTAAGGAGTCATTGAAA
ATCTCATGTGCAGCCTCTGGATTCACCTTCAGTAATGCTGCCATGTACTGGGTCCG
CCAGGCTCCAGGAAAGGGTCTGGAGTGGGTTGCTCGCATAAGAAGTAAACCTAATA
ATTATGCAACATATTATACTGATTCAGTGAAAGGCAGATTCACCATCTCCAGAGATG
ATTCAAAAAGCATGGTCCACCTACAAATGGATAACTTGAAAACTGAGGACACAGCC
ATGTATTACTGTACAGTAGGGGGCAACAACTACGCGGCTGCTTACTGGGGCCAAGG
CACTCTGGTCACTGTCTCTTCAGCCAAAACAACAGCCCCATCGGTCTATCCACTGG
CCCCTGTGTGTGGAGATACAACTGGCTCCTCGGTGACTCTAGGATGCCTGGTCAAG
GGTTATTTCCCTGAGCCAGTGACCTTGACCTGGAACTCTGGATCCCTGTCCAGTGG
TGTGCACACCTTCCCAGCTGTCCTGCAGTCTGACCTCTACACCCTCAGCAGCTCAG
TGACTGTAACCTCGAGCACCTGGCCCAGCCAGTCCATCACCTGCAATGTGGCCCAC
CCGGCAAGCAGCACCAAGGTGGAcAAGAAAATTGAGCCCAGAGGGCCCACAATCA
AGCCCTGTCCTCCATGCAAATGCCCAGCACCTAACCTCTTGGGTGGACCATCCGTC
TTCATCTTCCCTCCAAAGATCAAGGATGTACTCATGATCTCCCTGAGCCCCATAGTC
ACATGTGTGGTGGTGGATGTGAGCGAGGATGACCCAGATGTCCAGATCAGCTGGT
TTGTGAACAACGTGGAAGTACACACAGCTCAGACACAAACCCATAGAGAGGATTAC
AACAGTACTCTCCGGGTGGTCAGTGCCCTCCCCATCCAGCACCAGGACTGGATGA
GTGGCAAGGAGTTCAAATGCAAGGTCAACAACAAAGACCTCCCAGCGCCCATCGA
GAGAACCATCTCAAAACCCAAAGGGTCAGTAAGAGCTCCACAGGTATATGTCTTGC
CTCCACCAGAAGAAGAGATGACTAAGAAACAGGTCACTCTGACCTGCATGGTCACA
GACTTCATGCCTGAAGACATTTACGTGGAGTGGACCAACAACGGGAAAACAGAGC
TAAACTACAAGAACACTGAACCAGTCCTGGACTCTGATGGTTCTTACTTCATGTACA
GCAAGCTGAGAGTGGAAAAGAAGAACTGGGTGGAAAGAAATAGCTACTCCTGTTC
AGTGGTCCACGAGGGTCTGCACAATCACCACACGACTAAGAGCTTCTCCCGGACT
CCgGGTAAATGA

[Fig.9]

ATGAAAGTGCCTGTTAGGCTGCTGGTGCTGTTGTTTTGGATTCCAGCTTCCAGAAG
TGATGTTGTGTTGACACAAACTCCAGTTGCCCAGCCTGTCACACTTGGAGATCAAG
CTTCTATATCTTGCAGGTCTAGTCAGAGCCTGGTACATAGTAATGGAAACACTTATT
TGGAATGGTACCTACAGAAGCCAGGCCAGTCTCCACAGCTCCTCATCTATAAGGTT
TCCAACCGATTTTCTGGGGTACCAGACAGGTTCATTGGCAGTGGGTCAGGGTCAGA
TTTCACCCTCAAGATCAGCAGAGTAGAGCCTGAGGACTTGGGAGTTTATTACTGTT
TCCAAGTTACACATGATCCATTCACGTTCGGCTCAGGGACGAAGTTGGAAATAAAA
CGGGCTGATGCTGCACCAACTGTATCTATCTTCCCACCATCCACGGAACAGTTAGC
AACTGGAGGTGCCTCAGTCGTGTGCCTCATGAACAACTTCTATCCCAGAGACATCA
GTGTCAAGTGGAAGATTGATGGCACTGAACGACGAGATGGTGTCCTGGACAGTGT
TACTGATCAGGACAGCAAAGACAGCACGTACAGCATGAGCAGCACCCTCTCGTTGA
CCAAGGCTGACTATGAAAGTCATAACCTCTATACCTGTGAGGTTGTTCATAAGACAT
CATCCTCACCCGTCGTCAAGAGCTTCAACAGGAATGAGTGTTAG

[Fig.10]

MLVLQWVLVTALFQGVHCAVQLVESGGGLVQPKESLKISCAASGFTFSNAAMYWVRQAPG
KGLEWVARIRSKPNNYATYYTDSVKGRFTISRDDSKSMVHLQMDNLKTEDTAMYYCTVGG
NNYAAAYWGQGTLVTVSSAKTTAPSVYPLAPVCGDTTGSSVTLGCLVKGYFPEPVTLTWNS
GSLSSGVHTFPAVLQSDLYTLSSSVTVTSSTWPSQSITCNVAHPASSTKVDKKIEPRGPTIKPCP
PCKCPAPNLLGGPSVFIFPPKIKDVLMISLSPIVTCVVVDVSEDDPDVQISWFVNNVEVHTAQ
TQTHREDYNSTLRVVSALPIQHQDWMSGKEFKCKVNNKDLPAPIERTISKPKGSVRAPQVY
VLPPPEEEMTKKQVTLTCMVTDFMPEDIYVEWTNNGKTELNYKNTEPVLDSDGSYFMYSK
LRVEKKNWVERNSYSCSVVHEGLHNHHTTKSFSRTPGK

[Fig.11]

MKVPVRLLVLLFWIPASRSDVVLTQTPVAQPVTLGDQASISCRSSQSLVHSNGNTYLEWYLQ
KPGQSPQLLIYKVSNRFSGVPDRFIGSGSGSDFTLKISRVEPEDLGVYYCFQVTHDPFTFGSGT
KLEIKRADAAPTVSIFPPSTEQLATGGASVVCLMNNFYPRDISVKWKIDGTERRDGVLDSVT
DQDSKDSTYSMSSTLSLTKADYESHNLYTCEVVHKTSSSPVVKSFNRNEC

[Fig.12]

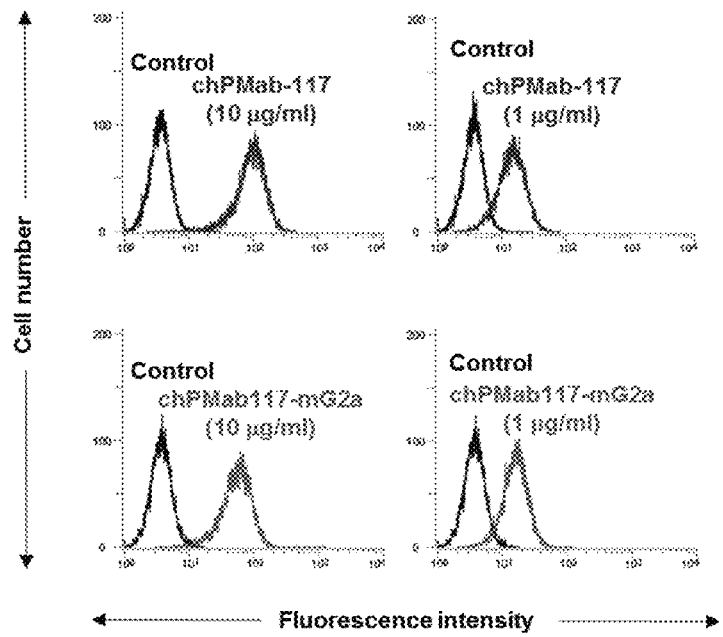

[Fig.13]
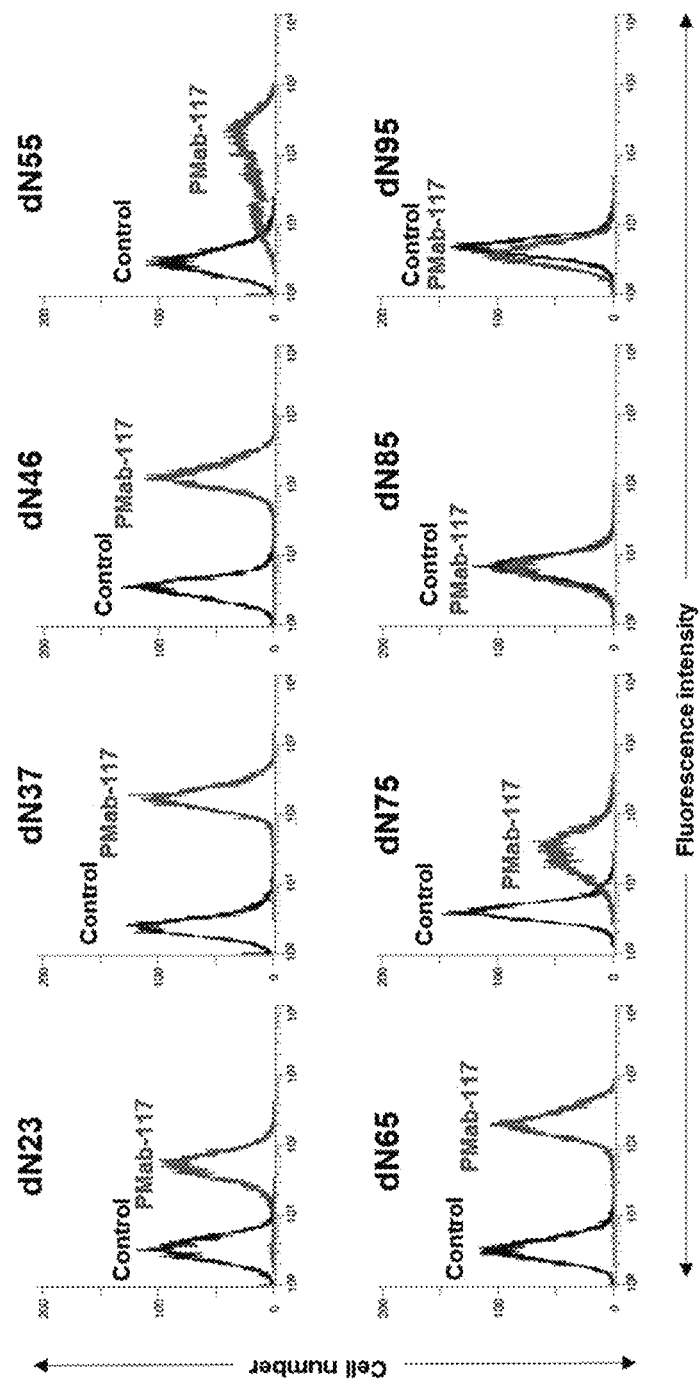

[Fig.14]
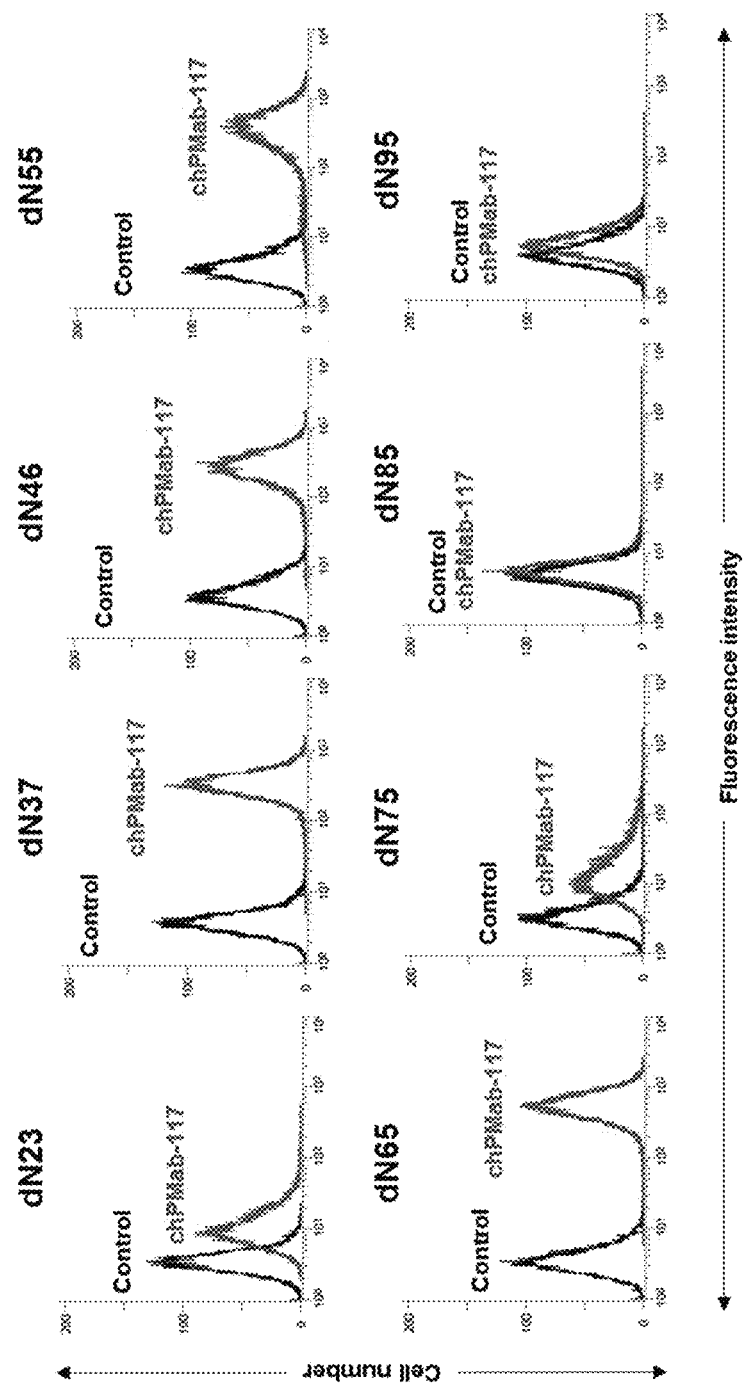

[Fig.15]
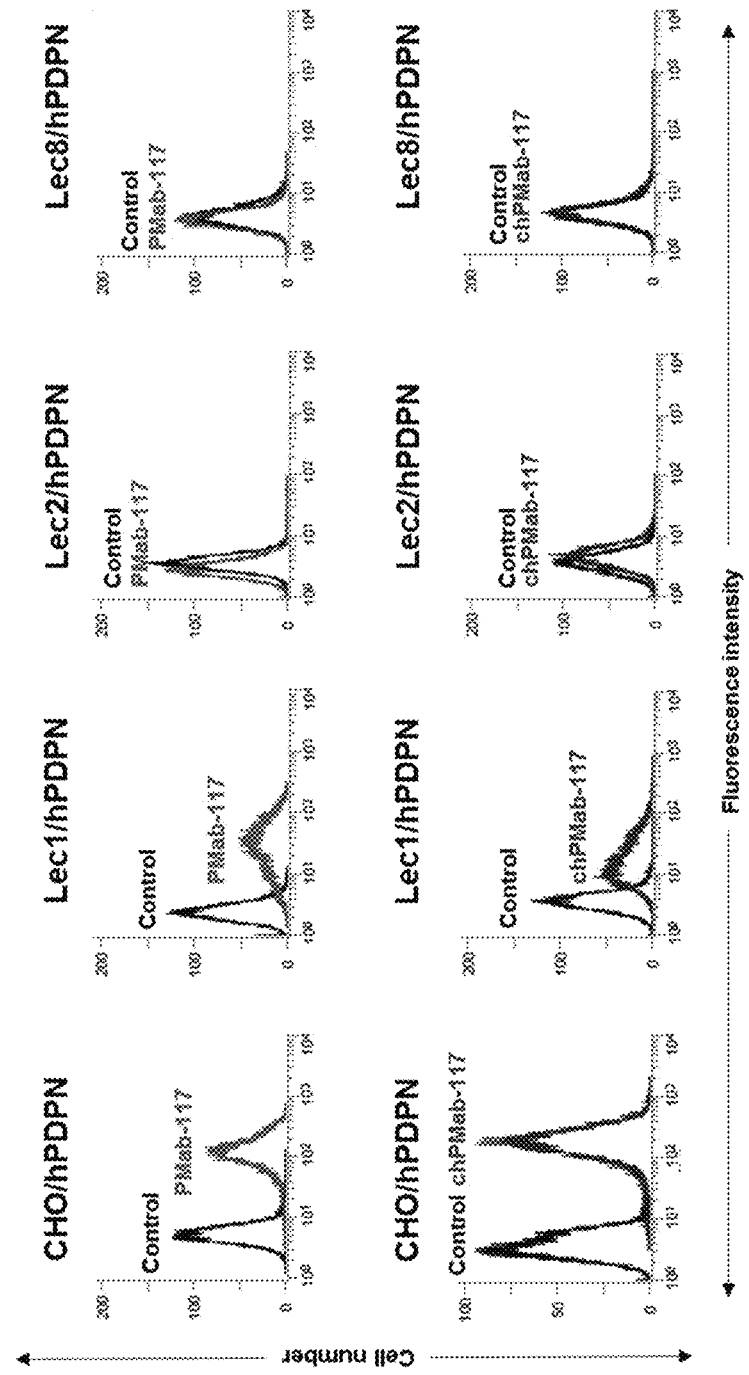

[Fig.16]
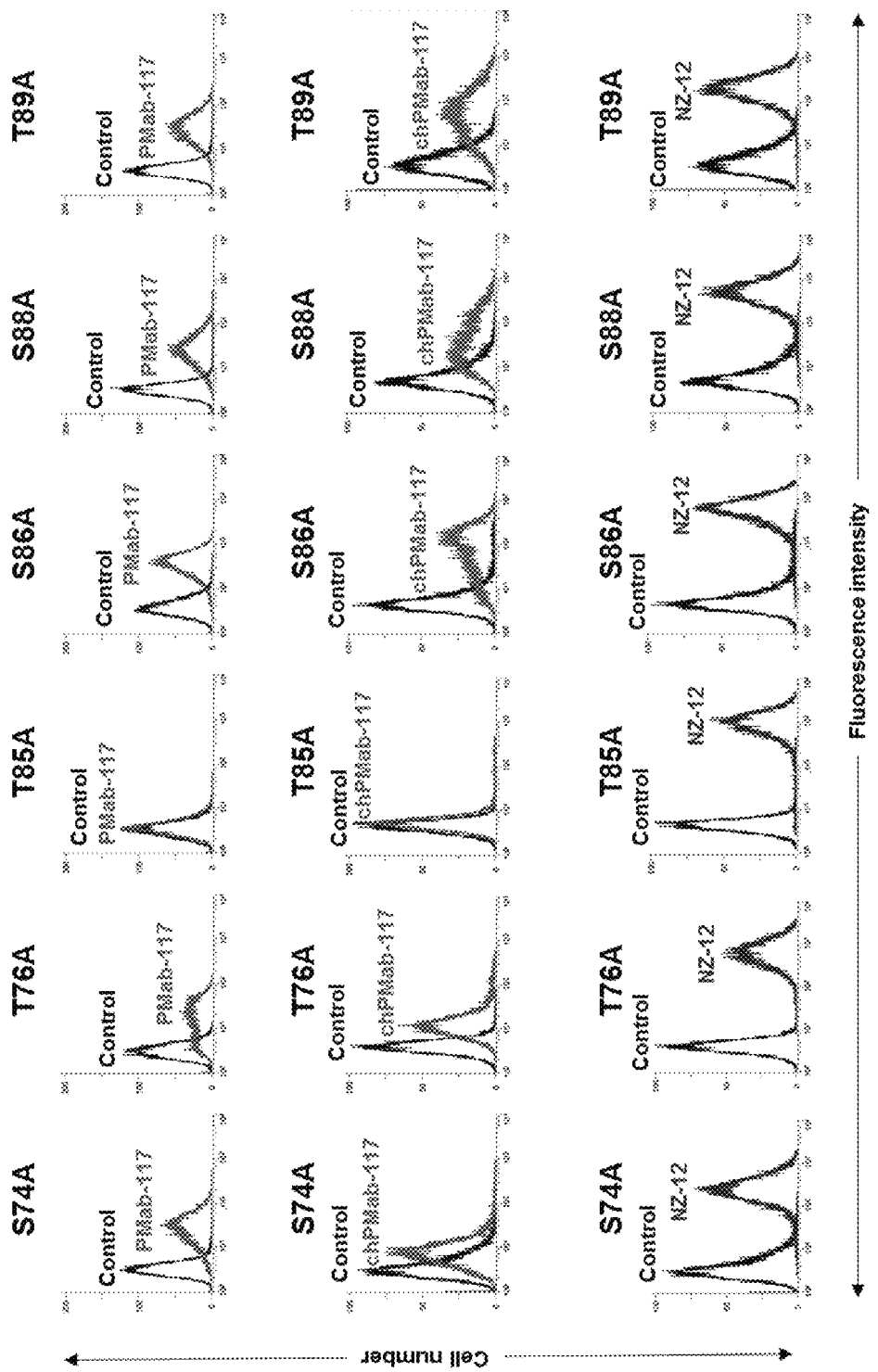

[Fig.17]
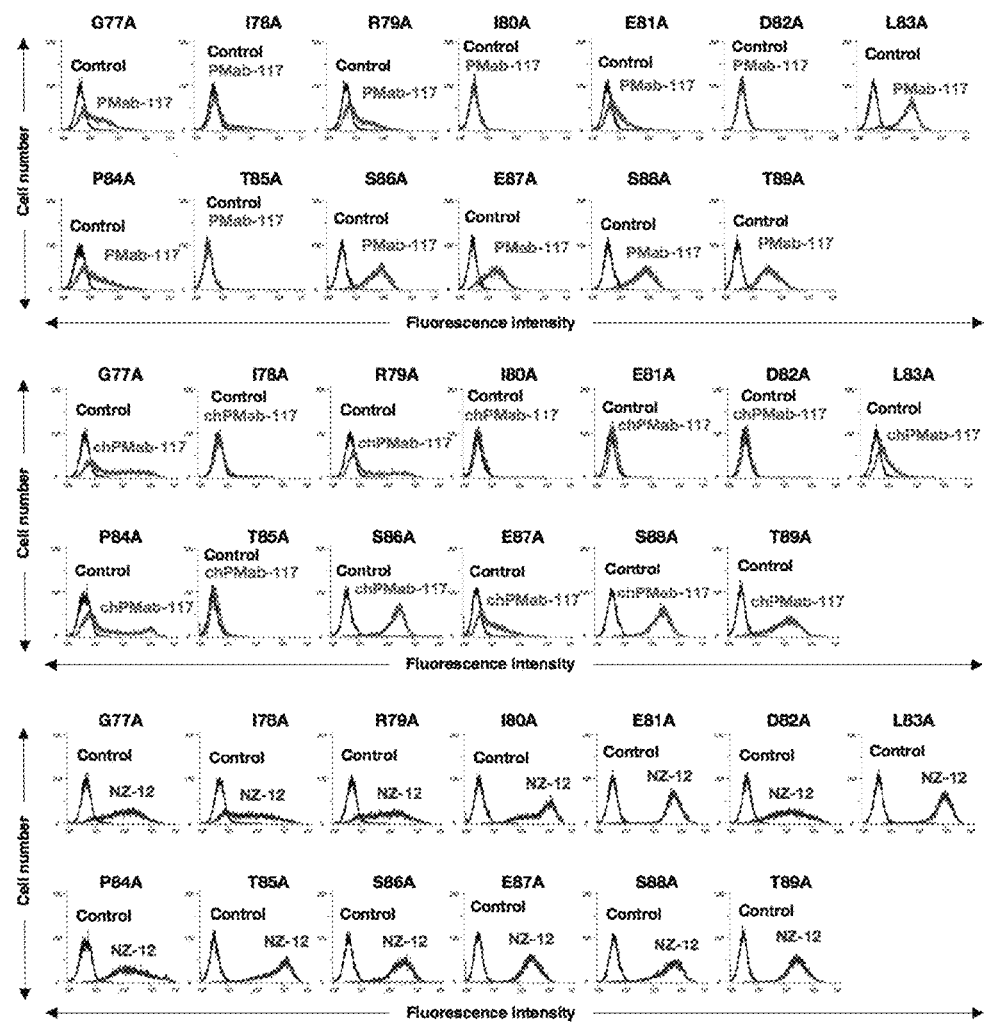

ANTI-PODOPLANIN ANTIBODY

TECHNICAL FIELD

The present invention relates to a novel anti-podoplanin antibody and the like.

BACKGROUND ART

Podoplanin is a mucin-type glycoprotein known as a platelet aggregating factor and a metastasis-accelerating factor and it is a type-1 transmembrane protein possessing a transmembrane domain at the C-terminus.

Podoplanin is known to exhibit high expression in brain tumor, mesothelioma, testicular tumor, ovarian cancer, and a variety of squamous cancers (oral cancer, pharynx cancer, larynx cancer, esophageal cancer, lung cancer, skin cancer, and uterine cervical cancer). Anti-podoplanin antibodies are therefore expected to show anti-cancer action (anti-tumor activity) in cancer (tumor) in which podoplanin is expressed highly. There is therefore a demand for an antibody having higher specificity or affinity to podoplanin or a novel antibody capable of recognizing podoplanin.

We have recently developed a method (CasMab method) of producing a monoclonal antibody showing specific reactivity with cancer cells. The CasMab method makes it possible to make use of a difference in post-translational modification such as glycan modification and thereby produce an antibody drug which attacks only a cancer cell when a membrane protein having the same amino acid sequence is expressed in cancer cells and normal cells (Non-Patent Documents 1 to 3).

A plurality of cancer cell-specific antibodies to podoplanin has so far been produced (Patent Document 1, Non-patent Documents 3 and 4). The cancer cell-specific antibodies to podoplanin show high reactivity with cancer cells such as lung cancer, esophageal cancer, brain tumor, and malignant mesothelioma in which cancer-type podoplanin is expressed highly, but they never react with lymphatic endothelial cells, alveolar epithelial cells, and renal epithelial cells in which normal podoplanin is highly expressed. Monoclonal antibodies so far developed by the CasMab method have strong ADCC/CDC activity and have shown a high anti-tumor effect in a mouse tumor xenograft model so that they have not only specificity to cancer but also possibility as an antibody drug.

CITATION LIST

Patent Document

Patent Document 1: WO2015/053381

Non-Patent Document

Non-Patent Document 1: Kato Y, Ogasawara S, Oki H, Goichberg P, Honma R, Fujii Y, Kaneko M K. LpMab-12 Established by CasMab Technology Specifically Detects Sialylated O-glycan on Thr52 of Platelet Aggregation-stimulating Domain of Human Podoplanin. PLoS One, 11(3), e0152912, 2016

Non-patent Document 2: Kato Y, Kunita A, Abe S, Ogasawara S, Fujii Y, Oki H, Fukayama M, Nishioka Y, and Kaneko M K. The chimeric antibody chLpMab-7 targeting human podoplanin suppresses pulmonary metastasis via ADCC and CDC rather than via its neutralizing activity. Oncotarget, 36003-36018, 2015

Non-patent Document 3: Kato Y and Kaneko M K. A Cancer-specific Monoclonal Antibody Recognizes the Aberrantly Glycosylated Podoplanin. Sci Rep., 4, 5924, 2014

Non-patent Document 4: Kaneko M K, Yamada S, Nakamura T, Abe S, Nishioka Y, Kunita A, Fukayama M, Fujii Y, Ogasawara S, Kato Y*. Antitumor activity of chLpMab-2, a human-mouse chimeric cancer-specific antihuman podoplanin antibody, via antibody-dependent cellular cytotoxicity. Cancer Med., DOI: 10.1002/cam4.1049

SUMMARY

Technical Problem

Technical problem of the present invention is to provide a novel anti-podoplanin antibody useful as a drug, a diagnostic agent, or a reagent.

Solution to Problem

It has been found that the epitope of a PMab-117 antibody and a modified antibody thereof established by the present invention contains an O-glycan (sialylated) added to Thr85 of human podoplanin. The PMab-117 antibody and modified antibody thereof are strongly positive to cancer cells in which human podoplanin is expressed, but have low reactivity with normal cells, showing that they are cancer cell-specific antibodies. It has never been certified that a glycan is added to Thr85 of human podoplanin and an antibody having an epitope containing O-glycan-added Thr85 has not been established at all so that PMab-117 is a cancer cell-specific anti-podoplanin antibody having a novel epitope.

The following is the details of the invention.

[1] A cancer cell-specific anti-podoplanin antibody or antigen-binding fragment thereof having an epitope in a Thr85-containing region in an amino acid sequence of human podoplanin represented by SEQ ID NO: 1, the Thr85 having a sialylated O-glycan added thereto.

[2] The cancer cell-specific anti-podoplanin antibody or antigen-binding fragment thereof as described above in [1], wherein the epitope is in a 78th to 85th region (IRIEDLPT) of the amino acid sequence of human podoplanin represented by SEQ ID NO: 1.

[3-1] A cancer cell-specific anti-podoplanin antibody or antigen-binding fragment thereof, including:
at least one of the following six CDR amino acid sequences,
at least one of amino acid sequences obtained by addition, substitution or deletion of one to several amino acids from the following six CDR amino acid sequences, or
at least one of amino acid sequences having 80% or more identity to the following six CDR amino acid sequences:

```
heavy chain CDR1:
                                    (SEQ ID NO: 2)
GFTFSNAAMY heavy chain CDR2:
                                    (SEQ ID NO: 3)
RIRSKPNNYATYYTDSVKG heavy chain CDR3:
                                    (SEQ ID NO: 4)
TVGGNNYAAAY
```

-continued

```
light chain CDR1:
                                       (SEQ ID NO: 5)
RSSQSLVHSNGNTYLE light chain CDR2:
                                       (SEQ ID NO: 6)
KVSNRFS light chain CDR3:
                                       (SEQ ID NO: 7)
FQVTHDPFT.
```

[3-2] The cancer cell-specific anti-podoplanin antibody or antigen-binding fragment thereof as described above in [1] or [2], including:

at least one of the following six CDR amino acid sequences, at least one of amino acid sequences obtained by addition, substitution or deletion of one to several amino acids from the following six CDR amino acid sequences, or at least one amino acid sequence having 80% or more identity to the following six CDR amino acid sequences:

```
heavy chain CDR1:
                                       (SEQ ID NO: 2)
GFTFSNAAMY heavy chain CDR2:
                                       (SEQ ID NO: 3)
RIRSKPNNYATYYTDSVKG heavy chain CDR3:
                                       (SEQ ID NO: 4)
TVGGNNYAAAY light chain CDR1:
                                       (SEQ ID NO: 5)
RSSQSLVHSNGNTYLE light chain CDR2:
                                       (SEQ ID NO: 6)
KVSNRFS light chain CDR3:
                                       (SEQ ID NO: 7)
FQVTHDPFT.
```

[4-1] A cancer cell-specific anti-podoplanin antibody or antigen-binding fragment thereof, including:

a heavy chain having an amino acid sequence represented by SEQ ID NO: 8 or 10;

a heavy chain having an amino acid sequence obtained by addition, substitution or deletion of one to several amino acids from the amino acid sequence represented by SEQ ID NO: 8 or 10;

a heavy chain having an amino acid sequence having 80% or more identity to the amino acid sequence represented by SEQ ID NO: 8 or 10;

a light chain having an amino acid sequence represented by SEQ ID NO: 9 or 11;

a light chain having an amino acid sequence obtained by addition, substitution or deletion of one to several amino acids from the amino acid sequence represented by SEQ ID NO: 9 or 11, or a light chain having an amino acid sequence having 80% or more identity to the amino acid sequence represented by SEQ ID NO: 9 or 11.

[4-2] The cancer cell-specific anti-podoplanin antibody or antigen-binding fragment thereof as described above in any of [1] to [3-2], including:

a heavy chain having an amino acid sequence represented by SEQ ID NO: 8 or 10;

a heavy chain having an amino acid sequence obtained by addition, substitution or deletion of one to several amino acids from the amino acid sequence represented by SEQ ID NO: 8 or 10;

a heavy chain having an amino acid sequence having 80% or more identity to the amino acid sequence represented by SEQ ID NO: 8 or 10, a light chain having an amino acid sequence represented by SEQ ID NO: 9 or 11;

a light chain having an amino acid sequence obtained by addition, substitution or deletion of one to several amino acids from the amino acid sequence represented by SEQ ID NO: 9 or 11; or a light chain having an amino acid sequence having 80% or more identity to the amino acid sequence represented by SEQ ID NO: 9 or 11.

[5] The cancer cell-specific anti-podoplanin antibody or antigen-binding fragment thereof as described above in any of [1] to [4-2], having one or more N-glycans bound to an Fc region thereof and no fucose bound to N-acetylglucosamin at a reducing end of the N-glycan(s).

[6] A nucleic acid encoding any one of the amino acid sequences as described above in [3] or [4].

[7] An expression vector including the nucleic acid described above in [6].

[8] A transformant including the expression vector described above in [7].

[9] A pharmaceutical composition including, as an effective ingredient thereof, the cancer cell-specific anti-podoplanin antibody or antigen-binding fragment thereof as described above in any of [1] to [5].

[10] A pharmaceutical composition including, as an effective ingredient thereof, the cancer cell-specific anti-podoplanin antibody or antigen-binding fragment thereof as described above in any of [1] to [5] to which a substance having an anti-cancer activity has been bound.

[11] The pharmaceutical composition described above in [9] or [10], which is a preventive or treatment agent of tumor.

[12] Human podoplanin having an amino acid sequence represented by SEQ ID NO: 1 and having Thr85 to which a sialylated O-glycan has been added.

[13] A glycopeptide having the following amino acid sequence: IRIEDLPT (SEQ ID NO: 12) and having Thr to which a sialylated O-glycan has been added.

Advantageous Effects of Invention

Using a cancer cell-specific antibody makes it possible to obtain a drug having a side effect minimized as much as possible because the antibody can exhibit an anticancer activity in a cancer cell-specific manner. It is also useful for the delivery of a cancer cell-targeting agent and is highly useful as a diagnostic agent or reagent.

The present invention makes it possible to provide a novel anti-podoplanin antibody useful as a drug, a diagnostic agent, and a reagent.

BRIEF DESCRIPTION OF DRAWINGS

FIG. 1 shows an amino acid sequence (SEQ ID NO: 1) of human podoplanin.

FIG. 2 shows measurement results, on EC800 (product of Sony), of fluorescence intensity in flow cytometry using PMab-117 and NZ-1.

FIG. 3 shows a heavy chain DNA sequence (SEQ ID NO: 13) of chPMab-117.

FIG. 4 shows a light chain DNA sequence (SEQ ID NO: 14) of chPMab-117.

FIG. 5 shows a heavy chain amino acid sequence (SEQ ID NO: 8) of chPMab-117.

FIG. 6 shows a light chain amino acid sequence (SEQ ID NO: 9) of chPMab-117.

FIG. 7 shows the measurement results, on EC800 (product of Sony), of fluorescence intensity in flow cytometry using chPMab-117.

FIG. 8 shows a heavy chain DNA sequence (SEQ ID NO: 15) of chPMab117-mG2a.

FIG. 9 shows a light chain DNA sequence (SEQ ID NO: 16) of chPMab117-mG2a.

FIG. 10 shows a heavy chain amino acid sequence (SEQ ID NO: 10) of chPMab117-mG2a.

FIG. 11 shows a light chain amino acid sequence (SEQ ID NO: 11) of chPMab117-mG2a.

FIG. 12 shows the measurement results, on EC800 (product of Sony), of fluorescence intensity in flow cytometry using chPMab117-mG2a.

FIG. 13 shows the measurement results, on EC800 (product of Sony), of fluorescence intensity in flow cytometry using PMab-117 in an N-terminal deletion mutant of human podoplanin.

FIG. 14 shows the measurement results, on EC800 (product of Sony), of fluorescence intensity in flow cytometry using chPMab-117 in an N-terminal deletion mutant of human podoplanin.

FIG. 15 shows the measurement results, on EC800 (product of Sony), of fluorescence intensity in flow cytometry using PMab-117 and chPMab-117 in various glycan-deficient cell lines of human podoplanin.

FIG. 16 shows the measurement results, on EC 800 (product of Sony), of fluorescence intensity in flow cytometry using PMab-117, chPMab-117, and NZ-1 in human podoplanin substituted, at all Ser/Thr on and after 75th one, with alanine.

FIG. 17 shows the measurement results, on EC 800 (product of Sony), of fluorescence intensity in flow cytometry using PMab-117, chPMab-117, and NZ-1 in human podoplanin substituted, at all of the 77th to 89th amino acids, with alanine.

DESCRIPTION OF EMBODIMENTS (Anti-Podoplanin Antibody)

An anti-podoplanin antibody according to the present invention is a cancer cell-specific anti-podoplanin antibody having an epitope in a Thr85-containing region of an amino acid sequence of human podoplanin represented by SEQ ID NO: 1 and in the antibody, Thr85 has a sialylated O-glycan added thereto. The O-glycan is also called an "O-linked glycan".

The term "antibody" as used herein has a structure which has two heavy chains (H chains) and two light chains (L chains) associated with each other and has been stabilized by a pair of disulfide bonds. The heavy chains are each composed of a heavy chain variable region VH, heavy chain constant regions CH1, CH2, and CH3, and a hinge region located between CH1 and CH2, while the light chains are each composed of a light chain variable region VL and a light chain constant region CL. Of these regions, a variable region fragment (Fv) composed of VH and VL is a region which is directly involved in antigen binding and provides the antibody with diversity. An antigen binding region composed of VL, CL, VH and CH1 is called "Fab region" and a region composed of the hinge region, CH2, and CH3 is called "Fc region".

Of the variable regions, the region in direct contact with the antigen is particularly highly variable and is called "complementarity-determining region (CDR)". A relatively mutation-less region other than CDR is called "framework region (FR)". The light chain variable region and the heavy chain variable region each have three CDRs (heavy chains CDR1 to 3 and light chains CDR1 to 3).

The anti-podoplanin antibody according to the present invention may be either a monoclonal antibody or a polyclonal antibody. The anti-podoplanin antibody of the present invention may be any isotype of IgG, IgM, IgA, IgD, and IgE.

The anti-podoplanin antibody according to the present invention may be obtained by immunizing a non-human animal such as mouse, rat, hamster, guinea pig, rabbit, or chicken or it may be a recombinant antibody, or a chimeric antibody, a humanized antibody, a fully humanized antibody, or the like. The "chimeric antibody" means an antibody obtained by linking fragments of antibodies derived from different species.

The term "humanized antibody" means an antibody obtained by substituting, by an amino acid sequence characteristic to a non-human-derived antibody, a position of a human antibody corresponding thereto. Examples of it include antibodies having heavy chains CDR1 to 3 and light chains CDR1 to 3 of the antibody prepared by immunizing a mouse or rat and, in all the other regions including four respective framework regions (FR) of the heavy chains and light chains, derived from the human antibody. Such an antibody may also be called "CDR grafted antibody". The term "humanized antibody" may include a human chimeric antibody.

The term "antigen-binding fragment" of the anti-podoplanin antibody as used herein means a fragment of the anti-podoplanin antibody that binds to podoplanin. Specific examples include, but are not limited to, Fab composed of VL, VH, CL, and CH1 regions; F(ab')2 having two Fabs connected via a disulfide bond in a hinge region; Fv composed of VL and VH; a single-chain antibody, scFv, having VL and VH connected via an artificial polypeptide linker; and a bispecific antibody such as diabody type, scDb type, tandem scFv type, and leucine zipper type.

The anti-podoplanin antibody according to the present invention has preferably an epitope in a glycopeptide portion of human podoplanin which is in a 78th to 85th region ($_{78}$-IRIEDLPT-$_{85}$) of an amino acid sequence of human podoplanin represented by SEQ ID NO: 1 and has 85th threonine to which a sialylated O-glycan has been added.

The anti-podoplanin antibody according to the present invention having an epitope in the 78th to 85th region ($_{78}$-IRIEDLPT-$_{85}$) of the amino acid sequence of human podoplanin is an antibody recognizes both a peptide and a glycan that are contained in the epitope.

The amino acid sequence represented by $_{78}$-IRIEDLPT-$_{85}$ corresponds to from 78th amino acid to 85th amino acid of human podoplanin represented by SEQ ID NO: 1 and T corresponds to 85th threonine (Thr85) of the amino acid sequence of SEQ ID NO: 1.

The present invention also provides, as an epitope of an anti-podoplanin antibody, a glycopeptide represented by IRIEDLPT (SEQ ID NO: 12) having Thr to which a sialylated O-glycan has been added. The present invention also provides a human podoplanin having an amino acid sequence represented by SEQ ID NO: 1 and having Thr85 to which a sialylated O-glycan has been added.

The anti-podoplanin antibody according to the present invention may have at least one of the following six CDRs. These CDRs are CDR sequences of PMab-117.

```
Heavy chain CDR1:
                                    (SEQ ID NO: 2)
GFTFSNAAMY Heavy chain CDR2:
                                    (SEQ ID NO: 3)
RIRSKPNNYATYYTDSVKG Heavy chain CDR3:
                                    (SEQ ID NO: 4)
TVGGNNYAAAY Light chain CDR1:
                                    (SEQ ID NO: 5)
RSSQSLVHSNGNTYLE Light chain CDR2:
                                    (SEQ ID NO: 6)
KVSNRFS Light chain CDR3:
                                    (SEQ ID NO: 7)
FQVTHDPFT
```

The anti-podoplanin antibody according to the present invention is a cancer cell-specific anti-podoplanin antibody having an epitope in a Thr85-containing region of an amino acid sequence of human podoplanin represented by SEQ ID NO: 1 and the Thr85 has a sialylated O-glycan added thereto. It has preferably at least one of the above-described six CDRs. The anti-podoplanin antibody has more preferably an epitope in a glycopeptide portion of human podoplanin which is in the 78th to 85th region ($_{78}$-IRIEDLPT-$_{85}$) of the amino acid sequence of human podoplanin represented by SEQ ID NO: 1 and has 85th threonine to which a sialylated O-glycan has been added.

The anti-podoplanin antibody according to the present invention may contain at least one of six CDRs. It may contain a plurality of CDRs of the six CDRs and for example, it may contain two or more, three or more, four or more, five or more or six CDRs.

When the anti-podoplanin antibody according to the present invention contains six CDRs, the anti-podoplanin antibody has heavy chains CDR1 to 3 represented by SEQ ID NOS: 2 to 4 and light chains CDR1 to 3 represented by SEQ ID NOS: 5 to 7, respectively.

When the anti-podoplanin antibody according to the present invention contains any one of heavy chains CDR1 to 3 represented by SEQ ID NOS: 2 to 4 and light chains CDR1 to 3 represented by SEQ ID NOS: 5 to 7, respectively, it may contain an amino acid sequence obtained by addition, substitution or deletion of one to several amino acids from the sequence.

In the present specification, the term "amino acid" is used in its broadest meaning and it embraces not only naturally occurring amino acids but also artificial amino acid variants and derivatives of them. The amino acids may be represented by a commonly used single-letter or three-letter code. Examples of the amino acid used herein include naturally occurring proteinogenic L-amino acids, non-naturally occurring amino acids, and chemically synthesized compounds having properties known in the art as characteristics of an amino acid.

Examples of the non-naturally occurring amino acids include, but are not limited to, α,α-disubstituted amino acids (such as α-methylalanine), N-alkyl-α-amino acids, D-amino acids, β-amino acids, and α-hydroxy acids, each having a main chain structure different from that of naturally occurring amino acids; amino acids (such as norleucine and homohistidine) having a side-chain structure different from that of naturally occurring amino acids; amino acids (such as "homo" amino acids, homophenylalanine, and homohistidine) having extra methylene in the side chain thereof; and amino acids (such as cysteic acid) obtained by substituting a carboxylic acid functional group in the side chain by a sulfonic acid group.

When the term "having addition, substitution, or deletion of one to several amino acids" is used herein, the number of amino acids to be added, substituted, or deleted is not particularly limited insofar as the resulting polypeptide retains its function as a CDR. The number of amino acids is set at, for example, 1, 2, 3, or 4. The term may mean "having addition, substitution, or deletion of one amino acid", "having addition, substitution, or deletion of one to two amino acids", "having addition, substitution, or deletion of one to three amino acids", or "having addition, substitution, or deletion of one to four amino acids".

The position of deletion, substitution, or addition of amino acid(s) may be any position of a CDR sequence to be subjected to addition, substitution, or deletion of amino acid(s) insofar as the function as a CDR is retained.

When the anti-podoplanin antibody according to the present invention contains any one of heavy chains CDR1 to 3 represented by SEQ ID NOS: 2 to 4 and light chains CDR1 to 3 represented by SEQ ID NOS: 5 to 7, respectively, it may contain an amino acid sequence having 80% or more identity to a corresponding amino acid sequence of heavy chains CDR1 to 3 represented by SEQ ID NOS: 2 to 4 and light chains CDR1 to 3 represented by SEQ ID NOS: 5 to 7, respectively.

The term "having 80% or more identity" as used herein means that when two polypeptides having an amino acid sequence before mutation and a sequence mutated therefrom, respectively, are aligned so that their amino acid sequences show the maximum identity, the number of amino acid residues which they have in common is 80% or more of the number of amino acids of the amino acid sequence before mutation.

The identity is not limited insofar as it is 80% or more and the function as a CDR can be retained. It can be set at, for example, 85% or more, 90% or more, 95% or more, 98% or more, or 99% or more.

The term "having 80% or more identity" to an amino acid sequence represented by any of SEQ ID NOS: 2 to 7 means that when an amino acid sequence represented by any of SEQ ID NOS: 2 to 7 and an amino acid sequence of a polypeptide having a sequence mutated therefrom are aligned so that they show the maximum identity as a result of comparison, the number of amino acid residues which they have in common is 80% or more of the number of amino acids of the amino acid sequence represented by any of SEQ ID NOS: 2 to 7.

A CDR composed of an amino acid sequence obtained by addition, substitution, or deletion of an amino acid from the amino acid sequence of the heavy chains CDR1 to 3 and the light chains CDR1 to 3, or a CDR having 80% or more identity to the amino acid sequence of the heavy chains CDR1 to 3 and the light chains CDR1 to 3 may be prepared using a known method such as site-specific mutagenesis, random mutagenesis, chain shuffling, or CDR walking. It is well known to those skilled in the art that when the above method is used, a CDR with more mature affinity can be obtained by presenting an antibody or antibody fragment having, in the CDR thereof, a variety of mutations on a phage surface by phage display, followed by screening using an antigen (e.g., Wu et al., PNAS, 95: 6037-6042 (1998); Schier, R. et al., J. Mol. Bio. 263: 551-567 (1996); Schier, R. et al., J. Mol. Biol. 255: 28-43 (1996); Yang, W. F. et al., J. Mol. Biol., 254: 392-403 (1995)).

The anti-podoplanin antibody according to the present invention preferably includes a heavy chain having an amino acid sequence represented by SEQ ID NO: 8 or 10; a heavy chain having an amino acid sequence obtained by addition, substitution, or deletion of one to several amino acids from the amino acid sequence represented by SEQ ID NO: 8 or 10; or a heavy chain having an amino acid sequence having 80% or more identity to the amino acid sequence represented by SEQ ID NO: 8 or 10.

The amino acid sequence represented by SEQ ID NO: 8 is the heavy chain amino acid sequence of a chimeric antibody chPMab-117 and the amino acid sequence represented by SEQ ID NO: 10 is the heavy chain amino acid sequence of a chimeric antibody chPMab-117-mG2a.

The anti-podoplanin antibody according to the present invention preferably includes a light chain having an amino acid sequence represented by SEQ ID NO: 9 or 11; a light chain having an amino acid sequence obtained by addition, substitution, or deletion of one to several amino acids from the amino acid sequence represented by SEQ ID NO: 9 or 11; or a light chain having an amino acid sequence having 80% or more identity to the amino acid sequence represented by SEQ ID NO: 9 or 11.

The amino acid sequence represented by SEQ ID NO: 9 is the light chain amino acid sequence of a chimeric antibody chPMab-117 and the amino acid sequence represented by SEQ ID NO: 11 is the light chain amino acid sequence of a chimeric antibody chPMab-117-mG2a.

The anti-podoplanin antibody according to the present invention more preferably includes the heavy chain having an amino acid sequence represented by SEQ ID NO: 8; and the light chain having an amino acid sequence represented by SEQ ID NO: 9.

It may include the heavy chain having an amino acid sequence obtained by addition, substitution or deletion of one to several amino acids from the amino acid sequence represented by SEQ ID NO: 8; and the light chain having an amino acid sequence obtained by addition, substitution or deletion of one to several amino acids from the amino acid sequence represented by SEQ ID NO: 9.

It may include the heavy chain having an amino acid sequence having 80% or more identity to the amino acid sequence represented by SEQ ID NO: 8 and the light chain having an amino acid sequence having 80% or more identity to the amino acid sequence represented by SEQ ID NO: 9.

The anti-podoplanin antibody according to the present invention more preferably includes the heavy chain having an amino acid sequence represented by SEQ ID NO: 10; and the light chain having an amino acid sequence represented by SEQ ID NO: 11.

It may include the heavy chain having an amino acid sequence obtained by addition, substitution, or deletion of one to several amino acids from the amino acid sequence represented by SEQ ID NO: 10; and the light chain having an amino acid sequence obtained by addition, substitution, or deletion of one to several amino acids from the amino acid sequence represented by SEQ ID NO: 11.

It may include the heavy chain having an amino acid sequence having 80% or more identity to the amino acid sequence represented by SEQ ID NO: 10 and the light chain having an amino acid sequence having 80% or more identity to the amino acid sequence represented by SEQ ID NO: 11.

When the term "addition, substitution, or deletion of one to several amino acids" from the amino acid sequence of a heavy chain or light chain is used herein, the number of amino acids to be added, substituted, or deleted can be set at, for example, 1, 2, 3, 4, 5, 6, 7, 8, 9, or 10. Other terms have the same meaning as described above.

The term "having 80% or more identity" to the amino acid sequence represented by any of SEQ ID NOS: 8 to 11 as used herein means that when two polypeptides having an amino acid sequence represented by any of SEQ ID NOS: 8 to 11 and a mutated sequence thereof, respectively, are aligned so that their amino acid sequences show the maximum identity as a result of comparison, the number of amino acid residues which they have in common is 80% or more of the number of the amino acids of the amino acid sequence represented by the any of SEQ ID NOS. 8 to 11.

The anti-podoplanin antibody according to the present invention may be an antibody having one or more N-glycans bound to the Fc region thereof and having no fucose bound to N-acetylglucosamine at the reducing end of the N-glycan. An N-glycan is also called an "N-linked glycan".

For example, the Fc region of an IgG antibody has therein two binding sites of an N-glycan and a complex-type glycan is bound to these sites. The term "N-glycan" means a glycan to be bound to Asn of an Asn-X-Ser/Thr sequence and has a common structure $Man_3GlcNAc_2$ (-Asn) bound to Asn. It is classified into a high mannose type, a hybrid type, a complex type, and the like, depending on the kind of the glycan bound to two mannoses (Man) at the non-reducing end.

Although fucose may bind to N-acetylglucosamine (GlcNAc) at the reducing end of an N-glycan, it is known that when fucose is not bound thereto, compared with when fucose is bound thereto, the resulting antibody has a remarkably enhanced ADCC activity. This is described, for example, in the pamphlet of WO2002/031140, the disclosure of which is incorporated by reference herein in its entirety.

When such an antibody having a remarkably enhanced ADCC activity is used, a dose of the antibody used as a drug can be decreased so that both alleviation of a side effect and a reduction in medical expenses can be achieved.

The anti-podoplanin antibody of the present invention may be used after a substance having an anti-cancer activity is bound thereto.

The term "substance having an anti-cancer activity" as used herein means a substance which causes at least one of reduction of a tumor size (retardation or stopping of a tumor from becoming large), inhibition of tumor metastasis, inhibition (retardation or stopping) of tumor growth, and alleviation of one or more symptoms associated with cancer. Specific examples include, but are not limited to, toxins, anti-cancer agents, and radioisotopes.

Examples of a toxin having an anti-cancer activity include *Pseudomonas* exotoxin (PE) or a cytotoxic fragment thereof (for example, PE38), a diphtheria toxin, and ricin A. The toxin having an anti-cancer activity exhibits toxicity only to cells into which the toxin is incorporated together with the anti-podoplanin antibody, that is, cancer cells expressing podoplanin so that it has an advantage of specifically producing an effect without adversely affecting cells around them. The anti-podoplanin antibody of the present invention is useful because it specifically binds to podoplanin that is expressed in tumor cells.

Examples of the anti-cancer agent include low molecular weight compounds such as adriamycin, daunomycin, mitomycin, cisplatin, vincristine, epirubicin, methotrexate, 5-fluorouracil, aclacinomycin, nitrogen mustard, cyclophosphamide, bleomycin, daunorubicin, doxorubicin, vincristine, vinblastine, vindesine, tamoxifen, and dexamethasone, and proteins such as cytokines activating immunocompetent cells (for example, human interleukin 2, human granulocyte-macrophage colony-stimulating factor, human macrophage colony-stimulating factor, and human interleukin 12).

Examples of the radioisotope having an anti-cancer activity include $^{32}P$, $^{14}C$, $^{125}I$, $^{3}H$, $^{131}I$, $^{211}At$, and $^{90}Y$. The radioisotope also exhibits toxicity to cells around cells to which the anti-podoplanin antibody binds, that is, podoplanin expressed cells. In general, tumor cells are not uniform and podoplanin is not expressed in every tumor cell so that a radioisotope is useful for killing podoplanin-negative tumor cells around them. Further, when a radioisotope is bound to an anti-podoplanin antibody, the antibody may be a low molecular weight one such as Fab or scFv.

The substance having an anti-cancer activity may be directly bound to the anti-podoplanin antibody by a known method. For example, the substance having an anti-cancer activity may be enclosed in a carrier such as liposome having a surface modified with the anti-podoplanin antibody.

When the substance having an anti-cancer activity is a protein or a polypeptide, a nucleic acid (which will be described later) encoding the anti-podoplanin antibody of the present invention may be linked with a DNA encoding the substance having an anti-cancer activity, followed by insertion into an appropriate expression vector to allow them to express as a fusion protein of the substance having an anti-cancer activity and the anti-podoplanin antibody.

(Nucleic Acid)

The present invention embraces a nucleic acid encoding the anti-podoplanin antibody of the present invention. The nucleic acid may be either a naturally occurring nucleic acid or an artificial nucleic acid. Examples include, but are not limited to, DNA, RNA, and a chimera of DNA and RNA. The base sequence of the nucleic acid encoding the anti-podoplanin antibody can be determined by a method known to those skilled in the art or a method based thereon. It can be prepared by a known method or a method based thereon.

The nucleic acid according to the present invention may be a nucleic acid encoding:

an amino acid sequence of the following six CDRs, an amino acid sequence obtained by addition, substitution, or deletion of one to several amino acids from the amino acid sequence of the following six CDRs, or an amino acid sequence having 80% or more identity to the amino acid sequence of the following six CDRs:

```
heavy chain CDR1:
                                    (SEQ ID NO: 2)
GFTFSNAAMY, heavy chain CDR2:
                                    (SEQ ID NO: 3)
RIRSKPNNYATYYTDSVKG, heavy chain CDR3:
                                    (SEQ ID NO: 4)
TVGGNNYAAAY, light chain CDR1:
                                    (SEQ ID NO: 5)
RSSQSLVHSNGNTYLE, light chain CDR2:
                                    (SEQ ID NO: 6)
KVSNRFS,
and light chain CDR3:
                                    (SEQ ID NO: 7)
FQVTHDPFT;
``` an amino acid sequence represented by SEQ ID NO: 8 or 10, an amino acid sequence obtained by addition, substitution, or deletion of one to several amino acids from the amino acid sequence represented by SEQ ID NO: 8 or 10, an amino acid sequence having 80% or more identity to the amino acid sequence represented by SEQ ID NO. 8 or 10, an amino acid sequence represented by SEQ ID NO: 9 or 11, an amino acid sequence obtained by addition, substitution, or deletion of one to several amino acids from the amino acid sequence represented by SEQ ID NO: 9 or 11, or an amino acid sequence having 80% or more identity to the amino acid sequence represented by SEQ ID NO: 9 or 11.

Examples of the nucleic acid encoding the anti-podoplanin antibody of the present invention include, but are not limited to, DNA encoding the heavy chain of chPMab-117 represented by SEQ ID NO: 13, DNA encoding the light chain of chPMab-117 represented by SEQ ID NO: 14, DNA encoding the heavy chain of chPMab117-mG2a represented by SEQ ID NO: 15, and DNA encoding the light chain of chPMab117-mG2a represented by SEQ ID NO: 16.

Respective nucleic acids encoding CDRs of chPMab-117 and chPMab117-mG2a are included in the DNA sequence represented by any of SEQ ID NOS: 13 to 16.

(Expression Vector)

The present invention also embraces an expression vector containing the nucleic acid of the present invention. The expression vector can be selected as needed according to a host cell to be used. Examples include a plasmid, a retrovirus vector, an adenovirus vector, an adeno-associated virus (AAV) vector, a plant virus vector such as cauliflower mosaic virus vector or tobacco mosaic virus vector, a cosmid, a YAC, and an EBV-derived episome. The nucleic acid of the present invention may be inserted into these expression vectors by a known method (such as a method using a restriction enzyme).

The expression vector of the present invention may further contain, in addition to the nucleic acid of the present invention, for example, a nucleic acid encoding the anti-podoplanin antibody of the present invention, a promoter for controlling the expression of an antibody gene, a replication origin, a selection marker gene, or the like. The promoter and the replication origin may be selected as needed, depending on the kind of the host cell and vector.

(Transformant)

The present invention embraces a transformant containing the vector of the present invention. The transformant can be obtained by transfecting the vector of the present invention into appropriate host cells. Examples of the usable host cells include eukaryotic cells such as mammalian cells (CHO cells, COS cells, myeloma cells, HeLa cells, Vero cells, and the like), insect cells, plant cells, and fungus cells (*Saccharomyces*, *Aspergillus*, and the like), and prokaryotic cells such as *Escherichia coli* (*E. coli*) and *Bacillus subtilis*.

(Production Method of Anti-Podoplanin Antibody)

Although no limitation is imposed on a production method of the anti-podoplanin antibody of the present invention, an anti-podoplanin monoclonal antibody can be obtained, for example, by isolating antibody producing cells from a non-human mammal immunized with podoplanin or a fragment thereof, fusing them with myeloma cells or the like to obtain hybridomas, and purifying an antibody produced by the hybridomas. An anti-podoplanin polyclonal antibody can be obtained from the serum of an animal immunized with podoplanin or fragment thereof. The anti-podoplanin antibody of the present invention may be obtained by immunizing a non-human mammal with podoplanin obtained by adding a glycan other than a glycan to be bound to Thr85.

The podoplanin or segment thereof used in the method of producing the anti-podoplanin antibody of the present invention has a Thr85-containing region in the amino acid sequence of human podoplanin represented by SEQ ID NO: 1 and the Thr85 has a sialylated O-glycan added thereto. It preferably has a 78th to 85th region (IRIEDLPT) in an amino acid sequence of human podoplanin represented by SEQ ID NO: 1 and Thr85 has a sialylated O-glycan added thereto.

When the anti-podoplanin antibody of the present invention is produced using genetic recombination, it may be produced, for example, by transforming a proper host with an expression vector containing a nucleic acid encoding the anti-podoplanin antibody of the present invention, culturing the resulting transformant under appropriate conditions to express an antibody, and then isolating and purifying by a known method.

Examples of the isolating and purifying method include an affinity column using protein A or the like, another chromatography column, a filter, ultrafiltration, salting-out, and dialysis. These methods may be used in combination as needed.

An antibody that binds to a predetermined epitope sequence can be produced using a method known to those skilled in the art or a method based thereon. For example, a peptide containing an epitope sequence is fixed to a solid phase carrier and binding between the peptide and a plurality of antibodies is detected. Then, an antibody that specifically binds to the epitope can be obtained.

As the "plurality of antibodies", antibodies obtained by immunizing an animal with an antigen protein or a partial peptide thereof may be used or an antibody library or an antibody fragment library constructed by phage display may be used. When a library constructed by phage display is used, it is also possible to fix a peptide containing an epitope sequence to a solid phase carrier, repeat panning, and thereby obtain an antibody that specifically binds to the epitope.

A human chimeric antibody and a human CDR grafted antibody can be produced by cloning an antibody gene from mRNA of a hybridoma producing an antibody of an animal other than human and linking it to a portion of a human antibody gene by using genetic recombination technology.

For the production of a human chimeric antibody, cDNA is synthesized using reverse transcriptase from mRNA of a hybridoma that produces a mouse antibody, the heavy chain variable region (VH) and the light chain variable region (LH) are cloned by PCR, and then the sequence is analyzed. Next, a 5' primer containing a leader sequence is prepared from an antibody base sequence having a high identity and then a portion of the cDNA from the signal sequence to the 3' end of the variable region is cloned by PCR using the 5' primer and the variable region 3' primer. On the other hand, the constant region of the heavy chain and the light chain of human IgG1 is cloned and for the heavy chain and the light chain, the mouse antibody-derived variable region and the human antibody-derived constant region are linked to each other and amplified by Overlapping Hanging using PCR. The DNA thus obtained is inserted into an appropriate vector, followed by transformation to obtain a human chimeric antibody.

For the production of a human CDR grafted antibody, a human antibody variable region having the highest homology with a mouse antibody variable region to be used is selected and cloned and the base sequence of CDR is altered by site-selective mutagenesis using a mega-primer method. When humanization of an amino acid sequence constituting a framework region disturbs specific binding to an antigen, an amino acid of a portion of the framework may be converted from a human type to a rat type.

A CDR composed of an amino acid sequence obtained by deletion, substitution or addition of one or two amino acids to the original amino acid sequence or a CDR composed of an amino acid sequence having 80% or more identity to the original amino acid sequence may be prepared using a known method such as site-specific mutagenesis, random mutagenesis, chain shuffling, or CDR walking.

It is well known to those skilled in the art that according to these methods, a CDR having more mature affinity can be obtained by presenting an antibody or antibody fragment having a variety of mutations in CDRs on the phage surface by phage display and screening using an antigen (for example, Wu et al., PNAS, 95: 6037-6042 (1998); Schier, R. et al., J. Mol. Bio. 263: 551-567 (1996); Schier, R. et al., J. Mol. Biol. 255: 28-43 (1996); Yang, W. P. et al., J. Mol. Biol., 254: 392-403 (1995)). The present invention also embraces an antibody containing a CDR matured in such a manner.

Additional examples of the antibody production method include the Adlib system for obtaining an antibody producing cell line from Trichostatin A-treated chicken B cell-derived DT40 cell line (Seo, H. et al., Nat. Biotechnol., 6: 731-736, 2002) and a method of producing a human antibody by immunizing KM mice obtained by destroying the mouse antibody gene and introducing a human antibody gene (Itoh, K. et al., Jpn. J. Cancer Res., 92: 1313-1321, 2001; Koide, A. et al., J. Mol. Biol., 284: 1141-1151, 1998). These methods can also be applied to the production of the antibody of the present invention.

The antigen-binding fragment of the anti-podoplanin antibody according to the present invention may be expressed by the above-described method using DNA encoding the fragment. Alternatively, a full-length antibody may be obtained and then treated with an enzyme such as papain or pepsin to fragment it.

The anti-podoplanin antibody according to the present invention may be different in amino acid sequence, molecular weight, isoelectric point, presence/absence of glycans, conformation or the like, depending on the production method or purification method. However, the antibody thus obtained is embraced in the present invention insofar as it has a function equivalent to that of the anti-podoplanin antibody of the present invention. For example, the anti-podoplanin antibody of the present invention expressed in a prokaryotic cell such as *E. coli* has a methionine residue added to the N-terminal of the amino acid sequence of the original antibody. The present invention also embraces such an antibody.

When the anti-podoplanin antibody of the present invention is an antibody having an N-glycan having no fucose bound to N-acetylglucosamine at the reducing end, such an antibody can be produced by a known method or a method based thereon. A method of producing such an antibody is described, for example, in WO2002/031140 or Japanese Patent Application Publication No. 2009-225781, the disclosure of which is incorporated herein by reference in its entirety.

Specifically, for example, an intended anti-podoplanin antibody can be obtained by transforming cells, whose enzymatic activity involved in the synthesis of GDP-fucose or α-1,6-fucosyltransferase activity has been reduced or deleted, by using a vector containing DNA encoding the anti-podoplanin antibody of the present invention, culturing the transformant thus obtained, and then purifying it.

Examples of the enzyme involved in synthesis of GDP-fucose include GDP-mannose 4,6-dehydratase (GMP), GDP-keto-6-deoxymannose 3,5-epimerase, 4-reductase (Fx), and GDP-beta-L-fucose pyrophosphorylase (GFPP).

Here, the cells are not particularly limited, but are preferably mammalian cells. For example, CHO cells having the above-described enzymatic activity reduced or deleted may be used.

Although the antibody composition obtained by the above method may contain an antibody having fucose bound to N-acetylglucosamine at the reducing end, the percentage of the fucose-bound antibody in the whole antibody is 20 wt % or less, preferably 10 wt % or less, more preferably 5 wt % or less, most preferably 3 wt % or less.

Further, the antibody having an N-glycan in which no fucose is bound to N-acetylglucosamine at the reducing end thereof may also be obtained by introducing a vector containing DNA encoding the anti-podoplanin antibody of the present invention into insect eggs, hatching and growing the insects, crossbreeding them if necessary to produce a transgenic insect, and extracting an anti-podoplanin antibody from the transgenic insect or a secretion thereof. As the insect, a silkworm may be used. In this case, the antibody can be extracted from silkworm cocoons.

Although the antibody composition obtained using the above method may also contain an antibody having fucose bound to N-acetylglucosamine at the reducing end, the percentage of the fucose-bound antibody in the whole antibody is 20 wt % or less, preferably 10 wt % or less, more preferably 5 wt % or less, most preferably 3 wt % or less.

(Activity of the Anti-Podoplanin Antibody of the Present Invention)

The drug efficacy mechanism of antibody drugs is based on two biological activities of an antibody. One of them is a target antigen-specific binding activity, which is an activity neutralizing the function of a target antigen molecule achieved by binding. Functional neutralization of the target antigen molecule is exhibited through a Fab region.

The other one is a biological activity of an antibody called "effector activity". The effector activity is exhibited as an antibody-dependent cellular cytotoxicity (ADCC), a complement-dependent cytotoxicity (CDC), direct induction of apoptosis, or the like through the Fc region of an antibody.

The activities of the anti-podoplanin antibody of the present invention can be measured in the following methods.

(1) Binding Activity

The binding activity of an antibody can be measured by a known method, for example, ELISA (enzyme-linked immunosorbent assay), EIA (enzyme immunoassay), RIA (radioimmunoassay), a fluorescent antibody method, or an FACS method.

(2) ADCC Activity

The term "ADCC activity" means the following activity: when the anti-podoplanin antibody of the present invention binds to the cell surface antigen of target cells, Fcγ receptor-bearing cells (effector cells) bind to the Fc portion thereof through an Fcγ receptor and damage the target cells.

The ADCC activity can be known by mixing target cells in which podoplanin is expressed, effector cells, and the anti-podoplanin antibody of the present invention, and measuring the degree of ADCC. As the effector cells, for example, mouse splenocytes, or monocytes isolated from the human peripheral blood or bone marrow may be used. As the target cells, for example, podoplanin-positive mesothelioma cells or podoplanin-positive glioblastoma cells may be used. The activity can be measured by labeling target cells with $^{51}$Cr or the like in advance, adding the anti-podoplanin antibody of the present invention to the resulting cells, incubating the resulting mixture, adding effector cells to the target cells at a ratio adequate therefor, incubating the resulting mixture, collecting the supernatant, and then counting the label in the supernatant.

(3) CDC Activity

The term "CDC activity" means cellular cytotoxicity caused by a complement system.

The CDC activity can be measured in a manner similar to that used in the ADCC activity test except for the use of a complement instead of the effector cells.

(4) Tumor Growth Inhibitory Activity

The tumor growth inhibitory activity can be measured using a tumor model animal. For example, a tumor is subcutaneously implanted into a mouse and the anti-podoplanin antibody of the present invention is administered thereto. A tumor growth inhibitory effect can be measured by comparing the volume of the tumor tissue between a non-administered group and an administered group.

The tumor growth inhibitory activity in the present invention may result from inhibition of the growth of individual cells or may result from induction of apoptosis.

(Pharmaceutical Composition)

The anti-podoplanin antibody of the present invention may be used for prevention or treatment of a tumor that expresses podoplanin. A pharmaceutical composition according to one aspect of the present invention contains the anti-podoplanin antibody or antigen-binding fragment thereof according to the present invention as an effective ingredient and further contains a pharmacologically acceptable carrier or additive.

The anti-podoplanin antibody of the present invention may be used for delivery of a drug targeting tumor cells. The pharmaceutical composition according to the present invention may contain, as an effective ingredient, an anti-podoplanin antibody or antigen-binding fragment thereof to which a substance having an anti-cancer activity has been bound and it may further contain a pharmacologically acceptable carrier or additive.

Examples of the carrier or additive include, but are not limited to, water, saline, phosphate buffers, dextrose, pharmaceutically acceptable organic solvents such as glycerol and ethanol, collagen, polyvinyl alcohol, polyvinylpyrrolidone, carboxy vinyl polymers, carboxymethylcellulose sodium, sodium polyacrylate, sodium alginate, water-soluble dextran, sodium carboxymethyl starch, pectin, methylcellulose, ethylcellulose, xanthan gum, gum arabic, casein, agar, polyethylene glycol, diglycerin, glycerin, propylene glycol, petrolatum, paraffin, stearyl alcohol, stearic acid, human serum albumin, mannitol, sorbitol, lactose, and surfactants.

The pharmaceutical composition of the present invention may be provided in a variety of forms, for example, a solution (for example, an injection), a dispersion, a suspension, a tablet, a pill, a powder, or a suppository. A preferred form is an injection and parenteral administration (for example, intravenous, transdermal, intraperitoneal, or intramuscular administration) of it is preferred.

The pharmaceutical composition of the present invention is effective for the treatment of podoplanin-related diseases such as tumors, thrombosis, and arteriosclerosis.

Examples of podoplanin-related tumors include brain tumor, mesothelioma, testicular tumor, ovarian cancer, and squamous cancer. Examples of the squamous cancer include, but are not limited to, oral cancer, pharynx cancer, larynx cancer, esophageal cancer, lung cancer, skin cancer, and uterine cervical cancer.

The present invention also embraces a method of treating a podoplanin-related disease, which method includes administering a therapeutically effective amount of the anti-podoplanin antibody of the present invention.

The term "therapeutically effective amount" as used herein means an amount of an active substance capable of alleviating one or more symptoms of a disease to be treated to a certain extent. For an anti-cancer agent, it means an amount that causes at least one of reduction of a tumor size, inhibition (retardation or stopping) of tumor metastasis, inhibition (retardation or stopping) of tumor growth, and alleviation of one or more symptoms associated with cancer.

Specifically, the dose of the anti-podoplanin antibody of the present invention may be, for example, from 0.025 to 50 mg/kg, preferably from 0.1 to 50 mg/kg, more preferably from 0.1 to 25 mg/kg, still more preferably from 0.1 to 10 mg/kg or from 0.1 to 3 mg/kg, but is not limited thereto.

(Marker and Diagnostic Agent)

Podoplanin is highly expressed in certain tumor cells. The anti-podoplanin antibody of the present invention is useful in the diagnosis of cancer, particularly cancer in which podoplanin is highly expressed, such as brain tumor, mesothelioma, testicular tumor, ovarian cancer, and a variety of squamous cancers (oral cancer, pharynx cancer, larynx cancer, esophageal cancer, lung cancer, skin cancer, and uterine cervical cancer). The anti-podoplanin antibody of the present invention specifically binds to tumor cells so that it is particularly useful for their diagnosis.

The present invention also embraces a diagnostic agent of cancer containing the anti-podoplanin antibody of the present invention, use of the anti-podoplanin antibody of the present invention for the diagnosis of cancer, and a diagnostic method of cancer using the anti-podoplanin antibody of the present invention.

All the disclosures of Patent Documents and Non-patent Documents cited herein are incorporated by reference in its entirety.

The details of the anti-podoplanin antibody of the present invention described herein can also be understood as those of an antigen-binding fragment of the anti-podoplanin antibody of the present invention instead of the anti-podoplanin antibody of the present invention.

Examples

The present invention will hereinafter be described specifically based on Examples and Comparative Examples. The present invention is not limited to or by Examples. Those skilled in the art can change the present invention into various aspects without departing from the significance of the present invention. Such a change is also embraced within the scope of the present invention.

1. Establishment of Anti-Podoplanin Antibody Having Novel Glycopeptide Epitope

Rats were each immunized with $1 \times 10^8$ LN229/hPDPN cells four times in total (once per 10 days). By ELISA (enzyme-linked immunosorbent assay), an antibody reacting with a recombinant protein purified from a cancer cell line was screened.

The cancer cell-specific anti-podoplanin antibody thus selected was named PMab-117 (rat IgM, kappa).

The recombinant protein was purified as described below.

Static culture of LN229/hPDPN cells was performed and 10 g of them in total was collected. To the resulting cells was added 10 mL of a 0.5% Triton/PBS solution and they were solubilized on ice by pipetting. The solution obtained by solubilization was centrifuged at 15,000 rpm for 30 minutes. The supernatant was added to 1 mL of an anti-FLAG antibody (M2) affinity column (product of Sigma Aldrich) and the resulting mixture was reacted at 4° C. for 18 hours. The reaction product was washed three times with 10 mL of PBS. The recombinant protein adsorbed to the column was eluted by adding a 0.1 mg/mL FLAG peptide (product of Sigma Aldrich) in 1-mL portions. The absorbance at OD280 was measured, the fraction thus eluted was concentrated, and the final concentration was adjusted to 0.1 mg/mL.

ELISA was performed as follows.

Podoplanin purified (1 mg/mL) was immobilized on a 96 well plate (Nunc MaxiSorp; product of Thermo Fisher) at 37° C. for 30 minutes, followed by blocking at 37° C. for 30 minutes with SuperBlock/PBST (product of Thermo Fisher). Similarly, a mouse hybridoma-derived culture supernatant and anti-rat IgG-HRP (product of Dako) were reacted successively under conditions of 37° C. and 30 minutes and color development was performed using TMB-Ultra (product of Thermo Fisher). The absorbance (OD: 655 nm) was measured using a microplate reader (product of Bio-Rad).

2. Flow Cytometry Using PMab-117

Reactivity of an anti-podoplanin antibody (PMab-117; rat IgM, kappa) with a podoplanin expressed cell line was studied by flow cytometry. First, PMab-117 (culture supernatant) was reacted at 4° C. for 30 minutes with various human podoplanin-expressed cell lines and then, reacted further with an anti-rat IgG-Oregon Green antibody (product of Thermo Fisher) at 4° C. for 30 minutes. As a negative control, only a secondary antibody was used.

Fluorescence intensity was measured using EC800 (product of Sony). The results are shown in FIG. 2.

PMab-117 shows high reactivity with podoplanin on cancer cells such as glioblastoma (LN319) or lung cancer (PC-10) but shows no reactivity with renal epithelial cells (HEK-293T). On the other hand, the anti-podoplanin antibody NZ-1 shows high reactivity with not only LN319 or PC-10 but also HEK-293T. The results have revealed that PMab-117 is a cancer cell-specific antibody.

3. Preparation of Human Chimeric PMab-117 (chPMab-117) and Determination of Amino Acid Sequence and Base Sequence of Antibody Gene From $1 \times 10^6$ hybridoma cells of an anti-podoplanin antibody (PMab-117, rat IgM, kappa), a total RNA was extracted using a QIAGEN RNeasy mini kit (product of QIAGEN). From 1 µg of the total RNA, cDNA synthesis was performed using a SuperScript III First-Strand Syntheses kit (product of Thermo Fisher). The cDNA was used as a template in the following experiment.

For the preparation of human chimeric PMab-117 (chPMab-117), a DNA encoding the VH region of PMab-117 was amplified by PCR and inserted into a pCAG vector having thereon a DNA encoding CH1, hinge, CH2 and CH3 regions of human IgG1 (pCAG-CHhG1/PMab-117HVH (G418)). A DNA encoding the VL region of PMab-117 was amplified by PCR and was inserted into a pCAG vector having thereon a DNA encoding the CK region of a human kappa chain (pCAG-hIgCKb/PMab-117LVL (zeocin)).

For amplification of the H chain, the following primers were used.

```
InF.HindIII-chP117H:
                                  (SEQ ID NO: 17)
CGGTATCGATAAGCTTAGTATGTTGGTGCTGCAG InFr.chP117HVH-BamHI:
                                  (SEQ ID NO: 18)
GGCCCTTGGTGGATCCTGAAGAGACAGTGACCAG
```

For amplification of the L chain, the following primers were used.

```
InF.HindIII-P117L:
                                  (SEQ ID NO: 19)
CGGTATCGATAAGCTTAAAATGAAAGTGCCTGTTAG InFr.chP117LVL-BamHI:
                                  (SEQ ID NO: 20)
ATGGTGCAGCGGATCCCCGTTTTATTTCCAACTTC
```

For PCR reaction, QIAGEN HotStar HiFidelity Polymerase Kit (product of QIAGEN) was used. The reaction was made under the following temperature conditions: first at 95° C. for 5 minutes, next 35 cycles of 94° C. for 15 seconds, 50° C. for one minute, and 72° C. for one minute, and then at 72° C. for 10 minutes. The amplified PCR product was purified in a QIAGEN PCR purification kit and the basic sequence was determined from the vector primer.

The amino acid sequence was predicted from the base sequence. The heavy chain DNA sequence, light chain DNA sequence, heavy chain amino acid sequence, and light chain amino acid sequence of chPMab-117 are shown as SEQ ID NOS: 13, 14, 8, and 9, respectively, in FIGS. 3 to 6.

<CDR of PMab-117>

The heavy chains CDR1 to 3 and the light chains CDR1 to 3 of PMab-117 had the following amino acid sequences as shown in SEQ ID NOS: 2 to 7.

```
Heavy chain CDR1:
                                  (SEQ ID NO: 2)
GFTFSNAAMY Heavy chain CDR2:
                                  (SEQ ID NO: 3)
RIRSKPNNYATYYTDSVKG Heavy chain CDR3:
                                  (SEQ ID NO: 4)
TVGGNNYAAAY Light chain CDR1:
                                  (SEQ ID NO: 5)
RSSQSLVHSNGNTYLE Light chain CDR2:
                                  (SEQ ID NO: 6)
KVSNRFS Light chain CDR3:
                                  (SEQ ID NO: 7)
FQVTHDPFT.
```

4. Flow Cytometry Using chPMab-117

Reactivity of human chimeric PMab-117 (chPMAb-117) with a podoplanin expressed cell line was studied by flow cytometry. First, chPMab-117 (10 µg/mL) was reacted at 4° C. for 30 minutes with various human podoplanin-expressed cell lines and further, the reaction products were each reacted with an anti-rat IgG-Oregon Green antibody (product of Thermo Fisher) and an anti-human IgG-FITC antibody (product of Thermo Fisher) at 4° C. for 30 minutes. As a negative control, only a secondary antibody was used.

Fluorescence intensity was measured using EC800 (product of Sony). The results are shown in FIG. 7.

The chPMab-117 shows high reactivity with podoplanin on cancer cells such as glioblastoma (LN319) or lung cancer (PC-10) but shows no reactivity with renal epithelial cells (HEK-293T) exhibiting strong podoplanin expression. Similar to the results of PMab-117 (FIG. 2), it has revealed that chPMab-117 is a cancer cell-specific antibody.

5. Preparation of Mouse Chimeric PMab-117 (chPMab117-mG2a)

The H-chain and L-chain variable regions of PMab-117 and the constant region of mouse IgG2a were inserted into a pCAG vector (product of InvivoGen) and a mouse chimeric PMab-117(chPMab117-mG2a) expression plasmid was prepared.

For amplification of the H chain, the following primers were used.

```
InF.HindIII-chP117H:
                                  (SEQ ID NO: 17)
CGGTATCGATAAGCTTAGTATGTTGGTGCTGCAG InFr.P117HVH-mG2a:
                                  (SEQ ID NO: 21)
GGCTGTTGTTTTGGCTGAAGAGACAGTGACCAGA
```

For amplification of the L chain, the following primers were used.

```
InF.HindIII-P117L:
                                  (SEQ ID NO: 19)
CGGTATCGATAAGCTTAAAATGAAAGTGCCTGTTAG InF.mIgCKter-NotI:
                                  (SEQ ID NO: 22)
TCTAGAGTCGCGGCCGCCTAACACTCATTCCTGT
```

The heavy chain DNA sequence, the light chain DNA sequence, the heavy chain amino acid sequence and the light chain amino acid sequence of chPMab117-mG2a are shown in FIGS. 8 to 11 as SEQ ID NOS: 15, 16, 10, and 11, respectively.

6. Flow Cytometry Using chPMab117-mG2a

Plasmids of the H chain and the L chain of chPMab117-mG2a were introduced into ExpiCHO cell lines (product of Thermo Fisher) by lipofection and a recombinant antibody of chPMab117-mG2a was expressed in the culture supernatant. The culture supernatant was collected two days after gene introduction. It was reacted with LN 319 cells at 4° C. for 30 minutes and was then reacted further with an anti-mouse IgG-FITC antibody (product of Thermo Fisher) at 4° C. for 30 minutes. As a negative control, only a secondary antibody was used.

The fluorescence intensity was measured using Cell Analyzer EC800 (product of Sony). The results are shown in FIG. 12.

Similar to chPMab117, chPMab117-mG2a shows high reactivity with podoplanin of glioblastoma cells (LN319).

7. Epitope Analysis 1 of PMab-117

Since PMab-117 was found to be a cancer specific antibody (CasMab), the recognition sequence (epitope) of it was analyzed.

The following are N-terminal deletion mutants of human podoplanin.

dN23: N-terminal 23rd amino acid full-length podoplanin.
dN37: N-terminal 37th amino acid deletion mutant.
dN46: N-terminal 46th amino acid deletion mutant.
dN55: N-terminal 55th amino acid deletion mutant.
dN65: N-terminal 65th amino acid deletion mutant.
dN75: N-terminal 75th amino acid deletion mutant.
dN85: N-terminal 85th amino acid deletion mutant.
dN95: N-terminal 95th amino acid deletion mutant.

The above deletion mutants were each reacted with PMab-117 (culture supernatant) and chPMab-117 (10 μg/mL) at 4° C. for 30 minutes and then reacted further with an anti-rat IgG-Oregon Green antibody (product of Thermo Fisher) and an anti-human IgG-FITC antibody (product of Thermo Fisher) at 4° C. for 30 minutes. As a negative control, only a secondary antibody was used.

The fluorescence intensity was measured using EC800 (product of Sony). The results are shown in FIGS. 13 and 14.

Disappearance of reactivity with dN85 (N-terminal 85th amino acid deletion mutant) has revealed that the N-terminal of the epitope of PMab-117 starts from between 75th to 85th amino acids.

8. Epitope Analysis 2 of PMab-117

Various glycan-deficient cell lines of human podoplanin were reacted with PMab-117 (culture supernatant) and chPMab-117 (10 μg/mL) at 4° C. for 30 minutes and then reacted further with an anti-rat IgG-Oregon Green antibody (product of Thermo Fisher) and an anti-human IgG-FITC antibody (product of Thermo Fisher) at 4° C. for 30 minutes. As a negative control, only a secondary antibody was used.

The fluorescence intensity was measured using EC800 (product of Sony). The results are shown in FIG. 15.

Reactivity with a sialic acid deficient cell line or galactose deficient cell line of human podoplanin disappeared, suggesting that the epitope of PMab-117 contains sialic acid added to an O-glycan.

9. Epitope Analysis 3 of PMab-117

Human podoplanin obtained by substituting all the Ser/Thr after 75th amino acid with alanine was reacted with each of PMab-117 (culture supernatant) and chPMab-117 (10 μg/ml) at 4° C. for 30 minutes and then reacted further with an anti-rat IgG-Oregon Green antibody (product of Thermo Fisher) and an anti-human IgG-FITC antibody (product of Thermo Fisher) at 4° C. for 30 minutes. As a negative control, only a secondary antibody was used and as a positive control, NZ-12 was used.

The fluorescence intensity was measured using EC800 (product of Sony). The results are shown in FIG. 16.

Disappearance of reactivity of PMab-117 with T85A has revealed that the epitope of PMab-117 contains Thr85.

10. Epitope Analysis 4 of PMab-117

Human podoplanin obtained by substituting all the 77th to 89th amino acids with alanine was reacted with each of PMab-117 (10 μg/mL) and chPMAb-117 (10 μg/mL) at 4° C. for 30 minutes and then reacted further with an anti-rat IgG-Oregon Green antibody (product of Thermo Fisher) and an anti-human IgG-FITC antibody (product of Thermo Fisher) at 4° C. for 30 minutes. As a negative control, only a secondary antibody was used and as a positive control, NZ-12 was used.

The fluorescence intensity was measured using EC800 (product of Sony). The results are shown in FIG. 17.

The reactivity of PMab-117 with I78A, I80A, D82A, and T85A disappeared, while the reactivity of PMab-117 with E81A became weak. The reactivity of chPMab-117 with I78A, I80A, E81A, D82A, and T85A disappeared. The results have revealed that the epitope of PMab-117 contains five amino acids, that is, Ile78, Ile80, Glu81, Asp82, and Thr85.

FIG. 15 shows that the epitope of PMab-117 contains a sialylated O-glycan and further, as shown in FIG. 16, Thr85 of human podoplanin is contained in the epitope of PMab-117. This suggests that Thr85 to which a sialylated O-glycan has been added is essential for the epitope of PMab-117. Further, amino acids around Thr85 were substituted with alanine and reactivity of PMab-117, chPMab-117, and NZ-12 was studied. FIG. 17 reveals that five amino acids, that is, Ile78, Ile80, Glu81, Asp82, and Thr85 are particularly important as the epitope of PMab-117.

It has been understood from the above results that a Thr85-containing glycopeptide of human podoplanin is an important target showing cancer specificity.

INDUSTRIAL APPLICABILITY

The anti-podoplanin antibody and antigen-binding fragment thereof according to the present invention are useful as a drug, a diagnostic agent, and a reagent and have industrial applicability.

[Sequence Listing Free Text]

SEQ ID NO: 1 represents the amino acid sequence of human podoplanin.

SEQ ID NO: 2 represents the amino acid sequence of heavy chain CDR1 of PMab-117.

SEQ ID NO: 3 represents the amino acid sequence of heavy chain CDR2 of PMab-117.

SEQ ID NO: 4 represents the amino acid sequence of heavy chain CDR3 of PMab-117.

SEQ ID NO: 5 represents the amino acid sequence of light chain CDR1 of PMab-117.

SEQ ID NO: 6 represents the amino acid sequence of light chain CDR2 of PMab-117.

SEQ ID NO: 7 represents the amino acid sequence of light chain CDR3 of PMab-117.

SEQ ID NO: 8 represents the heavy-chain amino acid sequence of chPMab-117.

SEQ ID NO: 9 represents the light-chain amino acid sequence of chPMab-117.

SEQ ID NO: 10 represents the heavy-chain amino acid sequence of chPMab117-mG2a.

SEQ ID NO: 11 represents the light-chain amino acid sequence of chPMab117-mG2a.

SEQ ID NO: 12 represents an amino acid sequence corresponding to the 78th to 85th region of the amino acid sequence of human podoplanin represented by SEQ ID NO: 1.

SEQ ID NO: 13 represents the heavy chain DNA sequence of chPMab-117.

SEQ ID NO: 14 represents the light chain DNA sequence of chPMab-117.

SEQ ID NO: 15 represents the heavy chain DNA sequence of chPMab117-mG2a.

SEQ ID NO: 16 represents the light chain DNA sequence of chPMab117-mG2a.

SEQ ID NO: 17 represents the primer InF.HindIII-chP117H used for amplification of the H chain.

SEQ ID NO: 18 represents the primer InFr.chP117HVH-BamHI used for amplification of the H chain.

SEQ ID NO: 19 represents the primer InF.HindIII-P117L used for amplification of the L chain.

SEQ ID NO: 20 represents the primer InFr.chP117LVL-BamHI used for amplification of the L chain.

SEQ ID NO: 21 represents the primer InFr.P117HVH-mG2a used for amplification of the H chain.

SEQ ID NO: 22 represents the primer InF.mIgCKter-NotI used for amplification of the L chain.

What is claimed is:

1. A cancer cell-specific anti-podoplanin antibody or antigen-binding fragment thereof, comprising the following six CDR amino acid sequences:

```
heavy chain CDR1:
                                    (SEQ ID NO: 2)
GFTFSNAAMY heavy chain CDR2:
                                    (SEQ ID NO: 3)
RIRSKPNNYATYYTDSVKG heavy chain CDR3:
                                    (SEQ ID NO: 4)
TVGGNNYAAAY light chain CDR1:
                                    (SEQ ID NO: 5)
RSSQSLVHSNGNTYLE light chain CDR2:
                                    (SEQ ID NO: 6)
KVSNRFS light chain CDR3:
                                    (SEQ ID NO: 7)
FQVTHDPFT.
```

2. The cancer cell-specific anti-podoplanin antibody or antigen-binding fragment thereof according to claim 1, having one or more N-glycans bound to an Fc region thereof and having no fucose bound to N-acetylglucosamine at a reducing end of the N-glycan(s).

3. A nucleic acid encoding the cancer cell-specific anti-podoplanin antibody or antigen-binding fragment thereof according to claim 1.

4. An expression vector, comprising the nucleic acid as claimed in claim 3.

5. A transformant, comprising the expression vector as claimed in claim 4.

6. A pharmaceutical composition, comprising, as an effective ingredient thereof, the cancer cell-specific anti-podoplanin antibody or antigen-binding fragment thereof as claimed in claim 1.

7. A pharmaceutical composition, comprising, as an effective ingredient thereof, the cancer cell-specific anti-podoplanin antibody or antigen-binding fragment thereof as claimed in claim 1 to which a substance having an anticancer activity has been bound.

8. A method of treating cancer, wherein said cancer expresses podoplanin, in a subject, which comprises administering to the subject the pharmaceutical composition according to claim 6.

9. A method of treating cancer, wherein said cancer expresses podoplanin, in a subject, which comprises administering to the subject the pharmaceutical composition according to claim 7.

10. A cancer cell-specific anti-podoplanin antibody or antigen-binding fragment thereof, comprising the following six CDR amino acid sequences:

```
heavy chain CDR1:
                                    (SEQ ID NO: 2)
GFTFSNAAMY, heavy chain CDR2:
                                    (SEQ ID NO: 3)
RIRSKPNNYATYYTDSVKG, heavy chain CDR3:
                                    (SEQ ID NO: 4)
TVGGNNYAAAY, light chain CDR1:
                                    (SEQ ID NO: 5)
RSSQSLVHSNGNTYLE, light chain CDR2:
                                    (SEQ ID NO: 6)
KVSNRFS,
and light chain CDR3:
                                    (SEQ ID NO: 7)
FQVTHDPFT;
``` wherein the heavy chain has an amino acid sequence that:
    is represented by SEQ ID NO: 8 or 10;
    is obtained by addition, substitution, or deletion of one to several amino acids from the amino acid sequence represented by SEQ ID NO: 8 or 10;
    has 80% or more identity to the amino acid sequence represented by SEQ ID NO: 8 or 10; and wherein the light chain has an amino acid sequence that:
    is represented by SEQ ID NO: 9 or 11;
    is obtained by addition, substitution or deletion of one to several amino acids from the amino acid sequence represented by SEQ ID NO: 9 or 11, or
    has 80% or more identity to the amino acid sequence represented by SEQ ID NO: 9 or 11.

11. The cancer cell-specific anti-podoplanin antibody or antigen-binding fragment thereof according to claim 10, having one or more N-glycans bound to an Fc region thereof and having no fucose bound to N-acetylglucosamine at a reducing end of the N-glycan(s).

12. A nucleic acid encoding the cancer cell-specific anti-podoplanin antibody or antigen-binding fragment thereof according to claim 10.

13. An expression vector, comprising the nucleic acid as claimed in claim 11.

14. A transformant, comprising the expression vector as claimed in claim 13.

15. A pharmaceutical composition, comprising, as an effective ingredient thereof, the cancer cell-specific anti-podoplanin antibody or antigen-binding fragment thereof as claimed in claim 10.

16. A pharmaceutical composition, comprising, as an effective ingredient thereof, the cancer cell-specific anti-podoplanin antibody or antigen-binding fragment thereof as claimed in claim 10 to which a substance having an anticancer activity has been bound.

17. A method of treating cancer, wherein said cancer expresses podoplanin, in a subject, which comprises administering to the subject the pharmaceutical composition according to claim 15.

18. A method of treating cancer, wherein said cancer expresses podoplanin, in a subject, which comprises administering to the subject the pharmaceutical composition according to claim 16.

* * * * *

UNITED STATES PATENT AND TRADEMARK OFFICE
CERTIFICATE OF CORRECTION

PATENT NO. : 11,306,152 B2
APPLICATION NO. : 16/498411
DATED : April 19, 2022
INVENTOR(S) : Kato et al.

It is certified that error appears in the above-identified patent and that said Letters Patent is hereby corrected as shown below:

On the Title Page

Under "OTHER PUBLICATIONS":
Line 23, change "39343946" to --3934–3946--.
Line 26, change "768777" to --768–777--.
Line 33, change "3600336018" to --36003–36018--.

In the Specification

Column 9, Line 6, change "W.F." to --W.P.--.

Signed and Sealed this
Sixteenth Day of August, 2022

Katherine Kelly Vidal
*Director of the United States Patent and Trademark Office*

SEQUENCE LISTING

```
<160> NUMBER OF SEQ ID NOS: 22

<210> SEQ ID NO 1
<211> LENGTH: 162
<212> TYPE: PRT
<213> ORGANISM: Homo sapiens

<400> SEQUENCE: 1

Met Trp Lys Val Ser Ala Leu Leu Phe Val Leu Gly Ser Ala Ser Leu
1               5                   10                  15

Trp Val Leu Ala Glu Gly Ala Ser Thr Gly Gln Pro Glu Asp Asp Thr
            20                  25                  30

Glu Thr Thr Gly Leu Glu Gly Gly Val Ala Met Pro Gly Ala Glu Asp
        35                  40                  45

Asp Val Val Thr Pro Gly Thr Ser Glu Asp Arg Tyr Lys Ser Gly Leu
    50                  55                  60

Thr Thr Leu Val Ala Thr Ser Val Asn Ser Val Thr Gly Ile Arg Ile
65                  70                  75                  80

Glu Asp Leu Pro Thr Ser Glu Ser Thr Val His Ala Gln Glu Gln Ser
                85                  90                  95

Pro Ser Ala Thr Ala Ser Asn Val Ala Thr Ser His Ser Thr Glu Lys
            100                 105                 110

Val Asp Gly Asp Thr Gln Thr Thr Val Glu Lys Asp Gly Leu Ser Thr
        115                 120                 125

Val Thr Leu Val Gly Ile Ile Val Gly Val Leu Leu Ala Ile Gly Phe
    130                 135                 140

Ile Gly Gly Ile Ile Val Val Met Arg Lys Met Ser Gly Arg Tyr
145                 150                 155                 160

Ser Pro

<210> SEQ ID NO 2
<211> LENGTH: 10
<212> TYPE: PRT
<213> ORGANISM: Artificial Sequence
<220> FEATURE:
<223> OTHER INFORMATION: PcMab-117 heavy chain CDR1

<400> SEQUENCE: 2

Gly Phe Thr Phe Ser Asn Ala Ala Met Tyr
1               5                   10

<210> SEQ ID NO 3
<211> LENGTH: 19
<212> TYPE: PRT
<213> ORGANISM: Artificial Sequence
<220> FEATURE:
<223> OTHER INFORMATION: PcMab-117 heavy chain CDR2

<400> SEQUENCE: 3

Arg Ile Arg Ser Lys Pro Asn Asn Tyr Ala Thr Tyr Tyr Thr Asp Ser
1               5                   10                  15

Val Lys Gly

<210> SEQ ID NO 4
<211> LENGTH: 11
```

```
<212> TYPE: PRT
<213> ORGANISM: Artificial Sequence
<220> FEATURE:
<223> OTHER INFORMATION: PcMab-117 heavy chain CDR3

<400> SEQUENCE: 4

Thr Val Gly Gly Asn Asn Tyr Ala Ala Ala Tyr
1               5                   10

<210> SEQ ID NO 5
<211> LENGTH: 16
<212> TYPE: PRT
<213> ORGANISM: Artificial Sequence
<220> FEATURE:
<223> OTHER INFORMATION: PcMab-117 light chain CDR1

<400> SEQUENCE: 5

Arg Ser Ser Gln Ser Leu Val His Ser Asn Gly Asn Thr Tyr Leu Glu
1               5                   10                  15

<210> SEQ ID NO 6
<211> LENGTH: 7
<212> TYPE: PRT
<213> ORGANISM: Artificial Sequence
<220> FEATURE:
<223> OTHER INFORMATION: PcMab-117 light chain CDR2

<400> SEQUENCE: 6

Lys Val Ser Asn Arg Phe Ser
1               5

<210> SEQ ID NO 7
<211> LENGTH: 9
<212> TYPE: PRT
<213> ORGANISM: Artificial Sequence
<220> FEATURE:
<223> OTHER INFORMATION: PcMab-117 light chain CDR3

<400> SEQUENCE: 7

Phe Gln Val Thr His Asp Pro Phe Thr
1               5

<210> SEQ ID NO 8
<211> LENGTH: 468
<212> TYPE: PRT
<213> ORGANISM: Artificial Sequence
<220> FEATURE:
<223> OTHER INFORMATION: chPcMab-117 heavy chain

<400> SEQUENCE: 8

Met Leu Val Leu Gln Trp Val Leu Val Thr Ala Leu Phe Gln Gly Val
1               5                   10                  15

His Cys Ala Val Gln Leu Val Glu Ser Gly Gly Gly Leu Val Gln Pro
            20                  25                  30

Lys Glu Ser Leu Lys Ile Ser Cys Ala Ala Ser Gly Phe Thr Phe Ser
        35                  40                  45

Asn Ala Ala Met Tyr Trp Val Arg Gln Ala Pro Gly Lys Gly Leu Glu
    50                  55                  60

Trp Val Ala Arg Ile Arg Ser Lys Pro Asn Asn Tyr Ala Thr Tyr Tyr
65                  70                  75                  80

Thr Asp Ser Val Lys Gly Arg Phe Thr Ile Ser Arg Asp Asp Ser Lys
                85                  90                  95

Ser Met Val His Leu Gln Met Asp Asn Leu Lys Thr Glu Asp Thr Ala
            100                 105                 110
```

Met Tyr Tyr Cys Thr Val Gly Gly Asn Asn Tyr Ala Ala Tyr Trp
            115                 120                 125

Gly Gln Gly Thr Leu Val Thr Val Ser Ser Gly Ser Thr Lys Gly Pro
        130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
                195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
                275                 280                 285

His Glu Asp Pro Glu Val Lys Phe Asn Trp Tyr Val Asp Gly Val Glu
                290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
                355                 360                 365

Val Tyr Thr Leu Pro Pro Ser Arg Asp Glu Leu Thr Lys Asn Gln Val
                370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
                435                 440                 445

Met His Glu Ala Leu His Asn His Tyr Thr Gln Lys Ser Leu Ser Leu
450                 455                 460

Ser Pro Gly Lys
465

<210> SEQ ID NO 9
<211> LENGTH: 238
<212> TYPE: PRT
<213> ORGANISM: Artificial Sequence
<220> FEATURE:
<223> OTHER INFORMATION: chPcMab-117 light chain

<400> SEQUENCE: 9

Met Lys Val Pro Val Arg Leu Leu Val Leu Leu Phe Trp Ile Pro Ala
1               5                   10                  15

Ser Arg Ser Asp Val Val Leu Thr Gln Thr Pro Val Ala Gln Pro Val
            20                  25                  30

Thr Leu Gly Asp Gln Ala Ser Ile Ser Cys Arg Ser Ser Gln Ser Leu
        35                  40                  45

Val His Ser Asn Gly Asn Thr Tyr Leu Glu Trp Tyr Leu Gln Lys Pro
    50                  55                  60

Gly Gln Ser Pro Gln Leu Leu Ile Tyr Lys Val Ser Asn Arg Phe Ser
65              70                  75                  80

Gly Val Pro Asp Arg Phe Ile Gly Ser Gly Ser Gly Ser Asp Phe Thr
                85                  90                  95

Leu Lys Ile Ser Arg Val Glu Pro Glu Asp Leu Gly Val Tyr Tyr Cys
            100                 105                 110

Phe Gln Val Thr His Asp Pro Phe Thr Phe Gly Ser Gly Thr Lys Leu
        115                 120                 125

Glu Ile Lys Arg Gly Ser Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 10
<211> LENGTH: 468
<212> TYPE: PRT
<213> ORGANISM: Artificial Sequence
<220> FEATURE:
<223> OTHER INFORMATION: chPMab117-mG2a heavy chain

<400> SEQUENCE: 10

Met Leu Val Leu Gln Trp Val Leu Val Thr Ala Leu Phe Gln Gly Val
1               5                   10                  15

His Cys Ala Val Gln Leu Val Glu Ser Gly Gly Gly Leu Val Gln Pro
            20                  25                  30

Lys Glu Ser Leu Lys Ile Ser Cys Ala Ala Ser Gly Phe Thr Phe Ser
        35                  40                  45

Asn Ala Ala Met Tyr Trp Val Arg Gln Ala Pro Gly Lys Gly Leu Glu
    50                  55                  60

Trp Val Ala Arg Ile Arg Ser Lys Pro Asn Asn Tyr Ala Thr Tyr Tyr
65              70                  75                  80

Thr Asp Ser Val Lys Gly Arg Phe Thr Ile Ser Arg Asp Ser Lys
                85                  90                  95

Ser Met Val His Leu Gln Met Asp Asn Leu Lys Thr Glu Asp Thr Ala
            100                 105                 110

Met Tyr Tyr Cys Thr Val Gly Gly Asn Asn Tyr Ala Ala Ala Tyr Trp
        115                 120                 125

Gly Gln Gly Thr Leu Val Thr Val Ser Ser Ala Lys Thr Thr Ala Pro
            130                 135                 140

Ser Val Tyr Pro Leu Ala Pro Val Cys Gly Asp Thr Thr Gly Ser Ser
145                 150                 155                 160

Val Thr Leu Gly Cys Leu Val Lys Gly Tyr Phe Pro Glu Pro Val Thr
                165                 170                 175

Leu Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Thr Ser Ser Thr Trp Pro Ser Gln Ser Ile Thr Cys Asn Val Ala His
    210                 215                 220

Pro Ala Ser Ser Thr Lys Val Asp Lys Lys Ile Glu Pro Arg Gly Pro
225                 230                 235                 240

Thr Ile Lys Pro Cys Pro Pro Cys Lys Cys Pro Ala Pro Asn Leu Leu
                245                 250                 255

Gly Gly Pro Ser Val Phe Ile Phe Pro Pro Lys Ile Lys Asp Val Leu
            260                 265                 270

Met Ile Ser Leu Ser Pro Ile Val Thr Cys Val Val Asp Val Ser
        275                 280                 285

Glu Asp Asp Pro Asp Val Gln Ile Ser Trp Phe Val Asn Asn Val Glu
    290                 295                 300

Val His Thr Ala Gln Thr Gln Thr His Arg Glu Asp Tyr Asn Ser Thr
305                 310                 315                 320

Leu Arg Val Val Ser Ala Leu Pro Ile Gln His Gln Asp Trp Met Ser
                325                 330                 335

Gly Lys Glu Phe Lys Cys Lys Val Asn Asn Lys Asp Leu Pro Ala Pro
            340                 345                 350

Ile Glu Arg Thr Ile Ser Lys Pro Lys Gly Ser Val Arg Ala Pro Gln
        355                 360                 365

Val Tyr Val Leu Pro Pro Pro Glu Glu Glu Met Thr Lys Lys Gln Val
    370                 375                 380

Thr Leu Thr Cys Met Val Thr Asp Phe Met Pro Glu Asp Ile Tyr Val
385                 390                 395                 400

Glu Trp Thr Asn Asn Gly Lys Thr Glu Leu Asn Tyr Lys Asn Thr Glu
                405                 410                 415

Pro Val Leu Asp Ser Asp Gly Ser Tyr Phe Met Tyr Ser Lys Leu Arg
            420                 425                 430

Val Glu Lys Lys Asn Trp Val Glu Arg Asn Ser Tyr Ser Cys Ser Val
        435                 440                 445

Val His Glu Gly Leu His Asn His His Thr Lys Ser Phe Ser Arg
    450                 455                 460

Thr Pro Gly Lys
465

<210> SEQ ID NO 11
<211> LENGTH: 238
<212> TYPE: PRT
<213> ORGANISM: Artificial Sequence
<220> FEATURE:
<223> OTHER INFORMATION: chPMab-117-mG2a light chain

<400> SEQUENCE: 11

Met Lys Val Pro Val Arg Leu Leu Val Leu Leu Phe Trp Ile Pro Ala
1               5                   10                  15

```
Ser Arg Ser Asp Val Val Leu Thr Gln Thr Pro Val Ala Gln Pro Val
            20                  25                  30

Thr Leu Gly Asp Gln Ala Ser Ile Ser Cys Arg Ser Ser Gln Ser Leu
        35                  40                  45

Val His Ser Asn Gly Asn Thr Tyr Leu Glu Trp Tyr Leu Gln Lys Pro
 50                  55                  60

Gly Gln Ser Pro Gln Leu Leu Ile Tyr Lys Val Ser Asn Arg Phe Ser
 65                  70                  75                  80

Gly Val Pro Asp Arg Phe Ile Gly Ser Gly Ser Gly Ser Asp Phe Thr
                 85                  90                  95

Leu Lys Ile Ser Arg Val Glu Pro Glu Asp Leu Gly Val Tyr Tyr Cys
            100                 105                 110

Phe Gln Val Thr His Asp Pro Phe Thr Phe Gly Ser Gly Thr Lys Leu
        115                 120                 125

Glu Ile Lys Arg Ala Asp Ala Ala Pro Thr Val Ser Ile Phe Pro Pro
130                 135                 140

Ser Thr Glu Gln Leu Ala Thr Gly Gly Ala Ser Val Val Cys Leu Met
145                 150                 155                 160

Asn Asn Phe Tyr Pro Arg Asp Ile Ser Val Lys Trp Lys Ile Asp Gly
                165                 170                 175

Thr Glu Arg Arg Asp Gly Val Leu Asp Ser Val Thr Asp Gln Asp Ser
            180                 185                 190

Lys Asp Ser Thr Tyr Ser Met Ser Ser Thr Leu Ser Leu Thr Lys Ala
        195                 200                 205

Asp Tyr Glu Ser His Asn Leu Tyr Thr Cys Glu Val Val His Lys Thr
    210                 215                 220

Ser Ser Ser Pro Val Val Lys Ser Phe Asn Arg Asn Glu Cys
225                 230                 235

<210> SEQ ID NO 12
<211> LENGTH: 8
<212> TYPE: PRT
<213> ORGANISM: Artificial Sequence
<220> FEATURE:
<223> OTHER INFORMATION: podoplanin 78 to 85 amino acid sequence
<220> FEATURE:
<221> NAME/KEY: CARBOHYD
<222> LOCATION: (8)..(8)

<400> SEQUENCE: 12

Ile Arg Ile Glu Asp Leu Pro Thr
1               5

<210> SEQ ID NO 13
<211> LENGTH: 1407
<212> TYPE: DNA
<213> ORGANISM: Artificial Sequence
<220> FEATURE:
<223> OTHER INFORMATION: chPMab-117 heavy chain

<400> SEQUENCE: 13
atgttggtgc tgcagtgggt tttggtgact gctcttttc aaggtgtgca ttgtgcggtg      60
cagcttgttg agtctggtgg aggattggtg cagcctaagg agtcattgaa atctctatgt     120
gcagcctctg gattcacctt cagtaatgct gccatgtact gggtccgcca ggctccagga    180
aagggtctgg agtggttgc tcgcataaga agtaaaccta ataattatgc aacatattat     240
actgattcag tgaaaggcag attcaccatc tccagagatg attcaaaaag catggtccac     300
```

-continued

```
ctacaaatgg ataacttgaa aactgaggac acagccatgt attactgtac agtaggggc     360 aacaactacg cggctgctta ctggggccaa ggcactctgg tcactgtctc ttcaggatcc    420
accaagggcc catcggtctt ccccctggca ccctcctcca agagcacctc tggggcaca     480 gcggccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct gggcaccca gacctacatc     660 tgcaacgtga atcacaagcc cagcaacacc aaggtggaca gaaagttga gcccaaatct     720 tgtgacaaaa ctcacacatg cccaccgtgc ccagcacctg aactcctggg gggaccgtca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca agccgcggg aggagcagta caacagcacg     960
taccgtgtgg tcagcgtcct caccgtcctg caccaggact ggctgaatgg caaggagtac   1020
aagtgcaagg tctccaacaa agccctccca gcccccatcg agaaaaccat ctccaaagcc   1080
aaagggcagc cccgagaacc acaggtgtac accctgcccc catcccggga tgagctgacc   1140
aagaaccagg tcagcctgac ctgcctggtc aaaggcttct atcccagcga catcgccgtg   1200
gagtgggaga gcaatgggca gccggagaac aactacaaga ccacgcctcc cgtgctggac   1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaatga                                        1407
```

<210> SEQ ID NO 14
<211> LENGTH: 717
<212> TYPE: DNA
<213> ORGANISM: Artificial Sequence
<220> FEATURE:
<223> OTHER INFORMATION: chPMab-117 light chain

<400> SEQUENCE: 14

```
atgaaagtgc tgttaggct gctggtgctg ttgttttgga ttccagcttc cagaagtgat       60
gttgtgttga cacaaactcc agttgcccag cctgtcacac ttggagatca agcttctata    120
tcttgcaggt ctagtcagag cctggtacat agtaatggaa cacttatttt ggaatggtac    180
ctacagaagc caggccagtc tccacagctc ctcatctata aggtttccaa ccgatttttct   240 ggggtaccag acaggttcat tggcagtggg tcagggtcag atttcaccct caagatcagc    300
agagtagagc ctgaggactt gggagtttat tactgtttcc aagttacaca tgatccattc    360
acgttcggct cagggacgaa gttggaaata aaacggggat ccgctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca aagtctacgc ctgcgaagtc    660
acccatcagg gcctgagctc gcccgtcaca aagagcttca cagggtgaga gtgttag      717
```

<210> SEQ ID NO 15
<211> LENGTH: 1407
<212> TYPE: DNA
<213> ORGANISM: Artificial Sequence
<220> FEATURE:
<223> OTHER INFORMATION: chPMab117-mG2a heavy chain

<400> SEQUENCE: 15

```
atgttggtgc tgcagtgggt tttggtgact gctcttttc aaggtgtgca ttgtgcggtg      60
cagcttgttg agtctggtgg aggattggtg cagcctaagg agtcattgaa atctcatgt     120
gcagcctctg gattcacctt cagtaatgct gccatgtact gggtccgcca ggctccagga    180
aagggtctgg agtgggttgc tcgcataaga agtaaaccta ataattatgc aacatattat    240
actgattcag tgaaaggcag attcaccatc tccagagatg attcaaaaag catggtccac    300
ctacaaatgg ataacttgaa aactgaggac acagccatgt attactgtac agtagggggc    360
aacaactacg cggctgctta ctggggccaa ggcactctgg tcactgtctc ttcagccaaa    420
acaacagccc catcggtcta tccactggcc cctgtgtgtg agatacaac tggctcctcg     480
gtgactctag gatgcctggt caagggttat ttccctgagc cagtgacctt gacctggaac    540
tctggatccc tgtccagtgg tgtgcacacc ttcccagctg tcctgcagtc tgacctctac    600
accctcagca gctcagtgac tgtaacctcg agcacctggc ccagccagtc catcacctgc    660
aatgtggccc acccggcaag cagcaccaag gtggacaaga aaattgagcc cagagggccc    720
acaatcaagc cctgtcctcc atgcaaatgc ccagcaccta acctcttggg tggaccatcc    780
gtcttcatct tccctccaaa gatcaaggat gtactcatga tctccctgag ccccatagtc    840
acatgtgtgg tggtggatgt gagcgaggat gacccagatg tccagatcag ctggtttgtg    900
aacaacgtgg aagtacacac agctcagaca caaacccata gagaggatta caacagtact    960
ctccgggtgg tcagtgccct ccccatccag caccaggact ggatgagtgg caaggagttc   1020
aaatgcaagg tcaacaacaa agacctccca gcgcccatcg agagaaccat ctcaaaaccc   1080
aaagggtcag taagagctcc acaggtatat gtcttgcctc caccagaaga gagatgact   1140
aagaaacagg tcactctgac ctgcatggtc acagacttca tgcctgaaga catttacgtg   1200
gagtggacca acaacgggaa aacagagcta aactacaaga acactgaacc agtcctggac   1260
tctgatggtt cttacttcat gtacagcaag ctgagagtgg aaaagaagaa ctgggtggaa   1320
agaaatagct actcctgttc agtggtccac gagggtctgc acaatcacca cacgactaag   1380
agcttctccc ggactccggg taaatga                                       1407
```

<210> SEQ ID NO 16
<211> LENGTH: 717
<212> TYPE: DNA
<213> ORGANISM: Artificial Sequence
<220> FEATURE:
<223> OTHER INFORMATION: chPMab-117-mG2a light chain

<400> SEQUENCE: 16

```
atgaaagtgc tgttaggct gctggtgctg ttgttttgga ttccagcttc cagaagtgat      60
gttgtgttga cacaaactcc agttgcccag cctgtcacac ttggagatca agcttctata    120
tcttgcaggt ctagtcagag cctggtacat agtaatggaa acacttattt ggaatggtac    180
ctacagaagc caggccagtc tccacagctc ctcatctata aggtttccaa ccgattttct    240
ggggtaccag acaggttcat tggcagtggg tcagggtcag atttcaccct caagatcagc    300
agagtagagc ctgaggactt gggagtttat tactgtttcc aagttacaca tgatccattc    360
acgttcggct cagggacgaa gttggaaata aaacgggctg atgctgcacc aactgtatct    420
atcttcccac catccaccga acagttagca actggaggtg cctcagtcgt gtgcctcatg    480
aacaacttct atcccagaga catcagtgtc aagtggaaga ttgatggcac tgaacgacga    540
```

```
gatggtgtcc tggacagtgt tactgatcag gacagcaaag acagcacgta cagcatgagc    600
agcaccctct cgttgaccaa ggctgactat gaaagtcata acctctatac ctgtgaggtt    660
gttcataaga catcatcctc acccgtcgtc aagagcttca acaggaatga gtgttag      717
```

<210> SEQ ID NO 17
<211> LENGTH: 34
<212> TYPE: DNA
<213> ORGANISM: Artificial Sequence
<220> FEATURE:
<223> OTHER INFORMATION: Primer InF.HindIII-chP117H

<400> SEQUENCE: 17

```
cggtatcgat aagcttagta tgttggtgct gcag                               34
```

<210> SEQ ID NO 18
<211> LENGTH: 34
<212> TYPE: DNA
<213> ORGANISM: Artificial Sequence
<220> FEATURE:
<223> OTHER INFORMATION: Primer InFr.chP117HVH-BamHI

<400> SEQUENCE: 18

```
ggcccttggt ggatcctgaa gagacagtga ccag                               34
```

<210> SEQ ID NO 19
<211> LENGTH: 36
<212> TYPE: DNA
<213> ORGANISM: Artificial Sequence
<220> FEATURE:
<223> OTHER INFORMATION: Primer InF.HindIII-P117L

<400> SEQUENCE: 19

```
cggtatcgat aagcttaaaa tgaaagtgcc tgttag                             36
```

<210> SEQ ID NO 20
<211> LENGTH: 35
<212> TYPE: DNA
<213> ORGANISM: Artificial Sequence
<220> FEATURE:
<223> OTHER INFORMATION: Primer InFr.chP117LVL-BamHI

<400> SEQUENCE: 20

```
atggtgcagc ggatccccgt tttatttcca acttc                              35
```

<210> SEQ ID NO 21
<211> LENGTH: 34
<212> TYPE: DNA
<213> ORGANISM: Artificial Sequence
<220> FEATURE:
<223> OTHER INFORMATION: Primer InFr.P117HVH-mG2a

<400> SEQUENCE: 21

```
ggctgttgtt ttggctgaag agacagtgac caga                               34
```

<210> SEQ ID NO 22
<211> LENGTH: 34
<212> TYPE: DNA
<213> ORGANISM: Artificial Sequence
<220> FEATURE:
<223> OTHER INFORMATION: Primer InF.mIgCKter-NotI

<400> SEQUENCE: 22

```
tctagagtcg cggccgccta acactcattc ctgt                               34
```